US011317898B2

(12) United States Patent
Kramer et al.

(10) Patent No.: US 11,317,898 B2
(45) Date of Patent: May 3, 2022

(54) BIOMATERIAL COLLECTION METHOD

(71) Applicant: WK Holdings, Inc., Monroe, NY (US)

(72) Inventors: Heidi Kramer, Monroe, NY (US); Herman Wagschal, Monroe, NY (US); Joseph Wagschal, Monroe, NY (US); Caleb Vainikka, Corcoran, MN (US); Braden Eliason, Shoreview, MN (US); Thomas E. Kramer, Andover, MN (US); Logan A. McDermot, Plymouth, MN (US); Brian J. Mullins, Minneapolis, MN (US); Matthew H. Rust, Hudson, WI (US); Dallas J. Erdahl, Elk River, MN (US)

(73) Assignee: WK Holdings Inc., Monroe, NY (US)

( * ) Notice: Subject to any disclaimer, the term of this patent is extended or adjusted under 35 U.S.C. 154(b) by 711 days.

(21) Appl. No.: 15/674,866

(22) Filed: Aug. 11, 2017

(65) Prior Publication Data

US 2019/0046164 A1    Feb. 14, 2019

(51) Int. Cl.
*A61B 10/00*    (2006.01)

(52) U.S. Cl.
CPC .... *A61B 10/007* (2013.01); *A61B 2560/0443* (2013.01); *A61B 2560/0462* (2013.01)

(58) Field of Classification Search
CPC .......... A61B 10/007; A61B 5/207–208; A61B 10/0096; A61B 10/0045; B01L 3/505; B01L 2200/0689; B01L 3/508–5088; A61F 5/451–4553; B67C 11/00–066; E03D 11/13–18; E03D 13/00–007; E03D 2201/00–40; A61G 9/00–02; A47K 11/00–12
See application file for complete search history.

(56) References Cited

U.S. PATENT DOCUMENTS

| 3,571,817 | A |   | 3/1971  | Gosnell |
| 3,815,646 | A |   | 6/1974  | Coakley |
| 3,943,770 | A | * | 3/1976  | McDonald ........... A61B 10/007 |
|           |   |   |         |           73/863.52 |
| 4,064,760 | A |   | 12/1977 | Benjamin |
| 4,067,335 | A |   | 1/1978  | Silvanov |

(Continued)

FOREIGN PATENT DOCUMENTS

| JP | 52-111035 A   | 7/1987 |
| JP | 1987111035 A  | 7/1987 |

(Continued)

OTHER PUBLICATIONS

International Search Report for International Application No. PCT/US2015/060181 dated Feb. 3, 2016.

(Continued)

*Primary Examiner* — Devin B Henson
*Assistant Examiner* — H. Q. Nguyen
(74) *Attorney, Agent, or Firm* — Merchant & Gould P.C.

(57) ABSTRACT

Apparatus and assemblies for automated sterile collection of urine and other biomaterials for medical testing, law enforcement testing, etc. Individual sample collection cartridges include an inflatable collection conduit and an inflatable collection vessel. The collection vessel can be sealed in multiple locations in a chronologically sequential manner to segregate an initial or "dirty" portion of a urine stream.

13 Claims, 32 Drawing Sheets

(56) References Cited

U.S. PATENT DOCUMENTS

| | | |
|---|---|---|
| 4,252,132 A | 2/1981 | Kuntz |
| 4,301,812 A | 11/1981 | Layton |
| 4,495,951 A | 1/1985 | Kenda |
| 4,569,090 A | 2/1986 | Muller |
| 4,636,474 A | 1/1987 | Ogura |
| 4,705,085 A | 11/1987 | Brown |
| 4,860,767 A | 8/1989 | Maekawa |
| 4,901,736 A | 2/1990 | Huang |
| 4,961,431 A | 10/1990 | Ikenaga |
| 4,962,550 A | 10/1990 | Ikenaga |
| 5,073,500 A | 12/1991 | Saito |
| 5,105,824 A | 4/1992 | Rasch |
| 5,111,539 A | 5/1992 | Hiruta |
| 5,184,359 A | 2/1993 | Tsukamura |
| 5,198,192 A | 3/1993 | Saito |
| 5,409,117 A | 4/1995 | Meador |
| 5,410,471 A | 4/1995 | Alyfuku |
| 5,652,911 A | 6/1997 | Van Venrooy et al. |
| 5,714,033 A | 2/1998 | Hayashi et al. |
| 5,720,054 A | 2/1998 | Nakayama et al. |
| 5,730,149 A | 3/1998 | Nakayama |
| 5,745,926 A | 5/1998 | Cailleteau |
| 5,758,917 A | 6/1998 | Langley |
| 5,785,044 A * | 7/1998 | Meador ............. A61B 10/007 206/221 |
| 5,920,916 A | 7/1999 | Norton |
| 6,052,842 A | 4/2000 | He |
| 6,079,058 A | 6/2000 | Green |
| 6,294,046 B1 | 9/2001 | Kume et al. |
| 6,342,704 B1 | 1/2002 | Jen et al. |
| 6,358,477 B1 | 3/2002 | Webb et al. |
| 6,402,702 B1 | 6/2002 | Gilcher |
| 6,493,884 B1 | 12/2002 | Muller et al. |
| 6,572,564 B2 | 6/2003 | Ito et al. |
| 6,607,166 B1 | 8/2003 | Pichkhadze |
| 6,684,414 B1 | 2/2004 | Rehrig |
| 6,775,852 B1 | 8/2004 | Alvarez et al. |
| 6,852,288 B2 | 2/2005 | Newberg |
| 7,195,602 B2 | 3/2007 | Yong et al. |
| 7,229,409 B2 | 6/2007 | Ito et al. |
| 7,291,309 B2 | 11/2007 | Watson et al. |
| 7,454,881 B2 | 11/2008 | Hanatani et al. |
| 7,785,304 B2 | 8/2010 | Kashmiran et al. |
| 7,819,821 B2 | 10/2010 | Forte et al. |
| 7,846,384 B2 | 12/2010 | Watson et al. |
| 8,328,733 B2 | 12/2012 | Forte et al. |
| 8,690,794 B1 | 4/2014 | Gallardo |
| 9,149,163 B2 | 10/2015 | Natt et al. |
| 9,155,525 B2 | 10/2015 | Lipinsky et al. |
| 2002/0193762 A1 | 12/2002 | Suydam |
| 2004/0138587 A1 | 7/2004 | Lyons, IV |
| 2005/0004538 A1 | 1/2005 | Forte |
| 2005/0142041 A1 | 6/2005 | Newberg |
| 2005/0261605 A1 | 11/2005 | Shemer et al. |
| 2007/0006368 A1 | 1/2007 | Key |
| 2007/0044213 A1 | 3/2007 | Hall |
| 2007/0270716 A1 | 11/2007 | Wu et al. |
| 2008/0312636 A1 | 12/2008 | Miller |
| 2009/0089919 A1 | 4/2009 | Rudolph |
| 2009/0216099 A1 | 8/2009 | Kim |
| 2009/0255045 A1 | 10/2009 | Sakurai |
| 2010/0269250 A1 | 10/2010 | Wilson et al. |
| 2010/0288059 A1 | 11/2010 | Viljoen et al. |
| 2010/0313818 A1 | 12/2010 | Cook |
| 2011/0051125 A1 | 3/2011 | Kim |
| 2011/0139276 A1 | 6/2011 | Kashmiran et al. |
| 2012/0046574 A1 | 2/2012 | Skakoon |
| 2013/0139474 A1 | 6/2013 | Coleman |
| 2013/0304008 A1 | 11/2013 | Hanuka |
| 2014/0216598 A1 | 8/2014 | Kashmirian et al. |
| 2014/0276214 A1 | 9/2014 | Lipinsky et al. |
| 2015/0223783 A1 | 8/2015 | Eschete et al. |
| 2015/0320404 A1 | 11/2015 | Kramer |
| 2015/0359522 A1 | 12/2015 | Recht et al. |
| 2018/0055489 A1 | 3/2018 | Kramer |
| 2018/0321218 A1 * | 11/2018 | Hall ............. A61B 10/007 |

FOREIGN PATENT DOCUMENTS

| | | |
|---|---|---|
| JP | 5-209996 A | 8/1993 |
| JP | 1993209996 A | 8/1993 |
| JP | 3-15255 A | 6/1994 |
| JP | 1996146509 A | 6/1994 |
| WO | 199518373 A1 | 7/1995 |
| WO | 199523337 A1 | 8/1995 |
| WO | 199609794 A1 | 4/1996 |
| WO | 199708993 A2 | 3/1997 |
| WO | 199727795 A1 | 8/1997 |
| WO | 199928724 A1 | 6/1999 |
| WO | 199959874 A1 | 11/1999 |
| WO | 200209493 A1 | 2/2002 |
| WO | 2002026096 A1 | 4/2002 |
| WO | 2002094104 A1 | 11/2002 |
| WO | 2003007771 A1 | 1/2003 |
| WO | 2004036343 A2 | 4/2004 |
| WO | 2005048842 A1 | 6/2005 |
| WO | 2007009170 A1 | 1/2007 |
| WO | 2008065325 A1 | 6/2008 |
| WO | 2009107988 A2 | 9/2009 |
| WO | 2009129638 A2 | 10/2009 |
| WO | 2010132800 A1 | 11/2010 |
| WO | 2011113164 A2 | 9/2011 |
| WO | 2011138728 A2 | 11/2011 |
| WO | 2011144950 A1 | 11/2011 |
| WO | 2012011127 A1 | 1/2012 |
| WO | 2014152626 A2 | 9/2014 |
| WO | 2016178711 A1 | 11/2016 |

OTHER PUBLICATIONS

"International Search Report and Written Opinion of the International Searching Authority for corresponding International Patent Application No. PCT/US2018/045817 dated Jan. 30, 2019".

* cited by examiner

FIG. 5
FIG. 6
FIG. 7
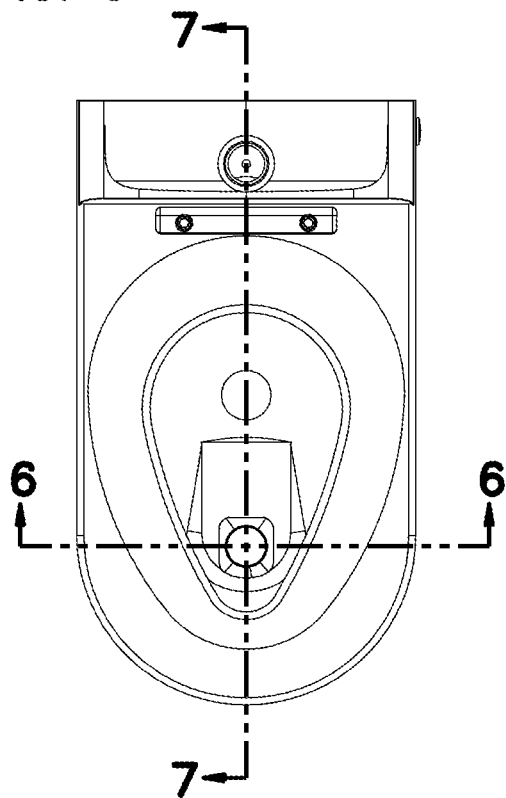
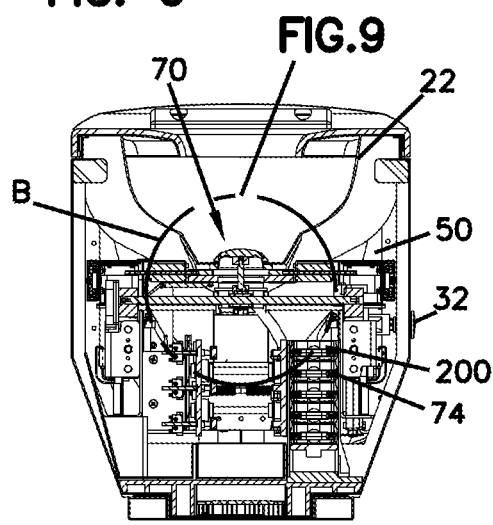
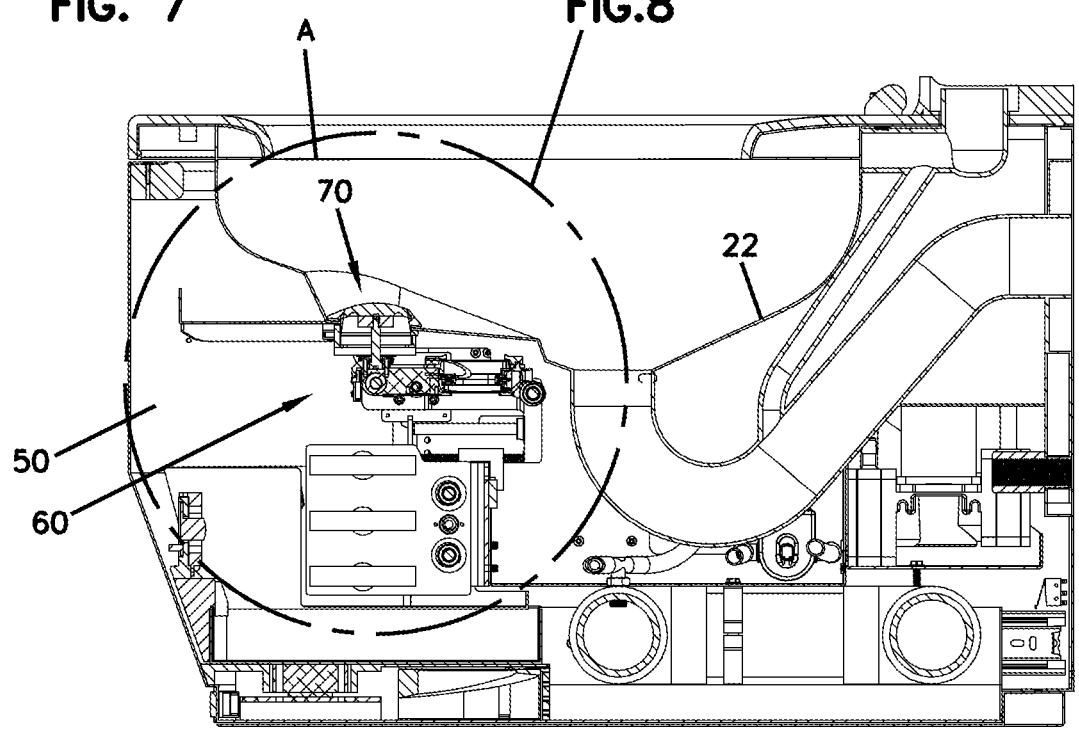

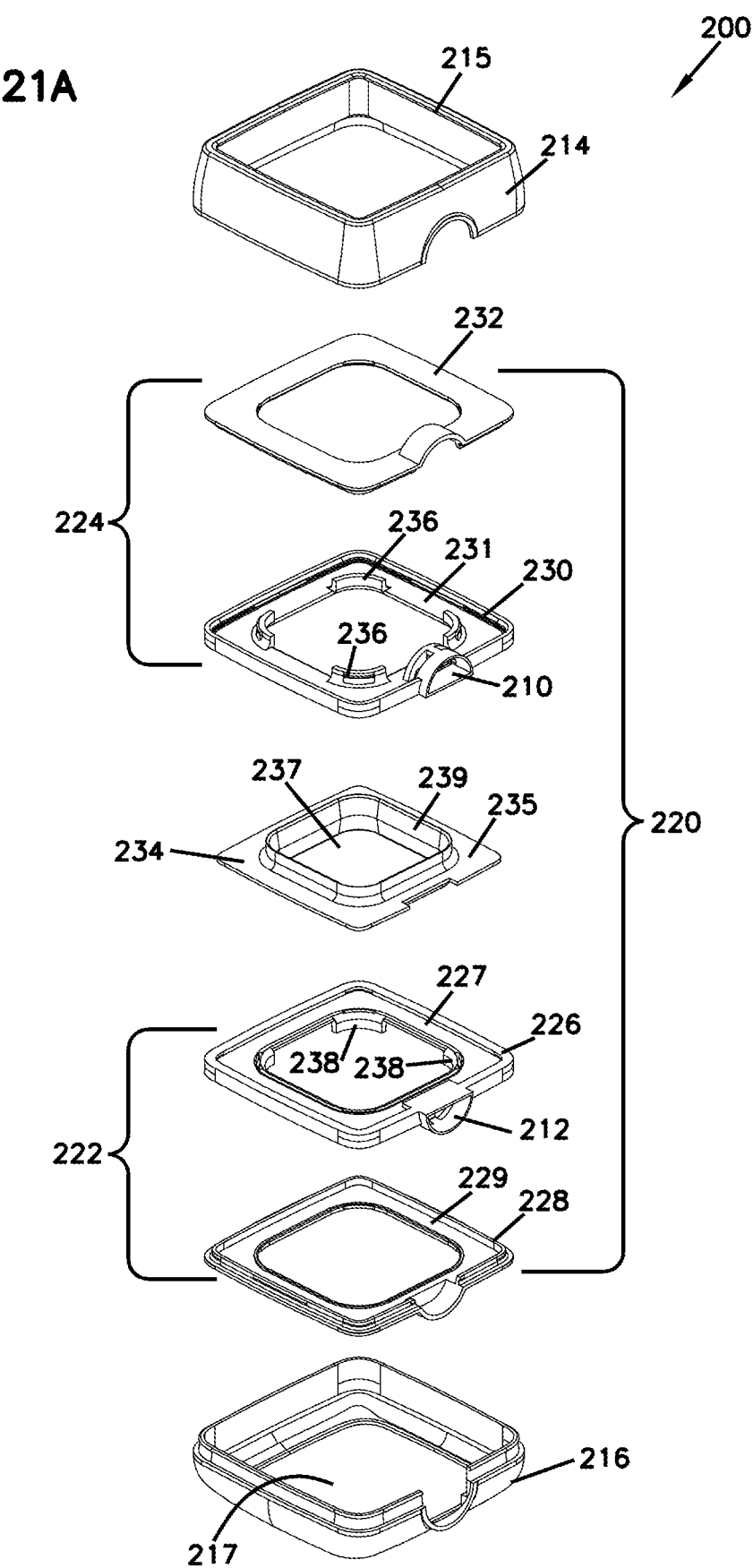

BIOMATERIAL COLLECTION METHOD

BACKGROUND

Biomaterials (e.g., urine, blood, feces) are routinely collected by medical and other professionals to test for any of a variety of biological conditions, diseases, drug or alcohol impairment, and so forth.

There is a need for improved systems for the collection and/or processing of biomaterial samples.

SUMMARY

In general terms the present disclosure is directed to a hands-free, biomaterial collection apparatus and/or its associated components and/or systems. In some examples, the collection apparatus is at least partially automated.

According to certain aspects of the present disclosure, a biomaterial collection apparatus includes a toilet bowl, the toilet bowl having an open top and defining two ports, a first of the ports in communication with a drainage or sewage system, and a second of the ports, or a collection port, that is openable and closable. Thus, the apparatus can be hooked up to the both a sewage system and a power source, such as an electricity grid, battery, or other form of electricity generator.

In some examples, the collection port is openable and closable with a plug. The plug can be electronically operated. Positioning of the plug can determine an operating status of the apparatus. When the plug is in place in the second port, the toilet can be flushed, and contents contained within the toilet bowl can exit the toilet bowl via the first port into the drainage/sewage system. In contrast, when the plug is removed from the collection port the apparatus can be used for biomaterial collection. Thus, in some examples, the collection port is adapted to receive and/or positionally align with a portion or portions of a biomaterial collection assembly.

According to further aspects of the present disclosure, a biomaterial collection system is provided. The biomaterial collection system can include one or more assemblies. In some examples, the biomaterial collection system is functionally integrated as part of a biomaterial collection apparatus that includes a toilet bowl.

Biomaterial collection systems in accordance with the present disclosure can include one or more biomaterial collection cartridges, or simply cartridges. A cartridge includes a housing defining first and second chambers. The first chamber is adapted to house or substantially house an expandable and collapsible biomaterial sample collection conduit, such as a funnel, in its collapsed state. The second chamber is adapted to house or substantially house an expandable and collapsible collection vessel, such as a bag, in its collapsed state.

In some examples, one or both of the collection conduit and the collection vessel is/are inflatable and the cartridge housing defines an air inlet in communication with at least one of the collection conduit or the collection vessel. In these examples, each of the collection vessel and the collection conduit defines one or more inflatable bladders having an inflation opening. In some examples, the cartridge housing defines two air inlets, one being in communication with an interior of the bladder or bladders of the inflatable collection vessel via its inflation opening, and the other being in communication with an interior of the bladder or bladders of the inflatable collection conduit via its inflation opening.

The cartridge housing can comprise a rigid shell made from, e.g., a rigid plastic. In some examples the rigid shell can include first and second shell pieces that are couplable to each other, e.g., via a snap fit or frictional fit or, alternatively, with a coupling medium, such as an adhesive. The first shell piece can define or partially define the first chamber and the second shell piece can define or partially define the second chamber.

In some examples, the cartridge includes an anchoring unit disposed between the first and second shell pieces and coupled to each of the shell pieces. The anchoring unit is adapted to anchor each of the collection vessel and the collection conduit to the cartridge and to couple and hermetically seal the inflation opening of each to its corresponding air inlet on the cartridge.

According to an example construction of the anchoring unit, the anchoring unit includes a vessel manifold and a conduit manifold. Each of the vessel manifold and the conduit manifold includes first and second frame members defining an air inlet and cooperating with each other and/or a divider component to anchor, respectively, the collection vessel and the collection conduit with a hermetic or substantially hermetic seal formed between the air inlet and the inflation opening. In some examples, one of the first and second frame members of each of the vessel manifold and the conduit manifold is adapted to securely couple to one of the shell pieces. In addition, the anchoring unit can include a divider that separates the vessel manifold from the conduit manifold and can aid in anchoring the collection vessel and the collection conduit.

According to further aspects of the present disclosure, a biomaterial collection system includes a sealing mechanism adapted to segregate a single biomaterial sample into a plurality of individually sealed containers. In some examples, the sealing mechanism is configured to seal off individually sealed containers of biomaterial sample in a chronologically sequential manner. Thus, for example, as the biomaterial sample is being collected, the sealing mechanism activates multiple times to segregate a first portion of the sample, and any number of subsequent portions of the sample, e.g., one, two, three, four, or more additional portions of the sample. One or more sensors, such as light/laser sensors, weight sensors, volume sensors, and/or heat sensors can be employed within the collection system to detect the progress of an ongoing biomaterial sample collection and effect a triggering of the sealing mechanism at the appropriate time or times, e.g., as each sample portion is collected.

In particular applications, the system is configured to collect urine samples for urinalysis and the sequentially triggered sealing mechanism segregates an initial urine collection volume from one or more subsequent urine collection volumes for a given urine sample. For a given urine sample, an initial portion of the urine stream is typically considered "dirty," i.e., non-representative of the actual composition of the patient's/subject's urine. Thus, patients are often asked to capture a "mid-stream" urine sample for analysis, and to discard the initial stream.

The biomaterial collection apparatus of the present disclosure can include additional components and/or features. For example, the biomaterial collection apparatus can have integrated therewith one or more of: a cartridge conveyance assembly for transporting cartridges or portions of cartridges between different locations or areas of the apparatus; a plug conveyance assembly for removing and replacing a plug in the collection port; a pneumatic system for inflating the inflatable collection conduit(s) and/or the inflatable collection vessels; a sample retrieving receptacle from which collected samples can be retrieved for analysis; a waste receptacle from which portions of used cartridges can be retrieved and discarded; one or more cutting mechanisms for cutting one or more sealed sample portions from a remaining portion of a collection vessel; one or more sensors for determining sample collection status and/or the status or positioning of various components of the apparatus; a sample labeling system for automated printing and applying of labels to collected biomaterial samples; a temperature control system (e.g., a refrigeration and/or heating system) for maintaining collected biomaterial samples at a desired temperature or within a desired range of temperatures; machinery, including, e.g., one or more motors (e.g., stepper motors), drivers, solenoids, actuators, etc., for automated movement of various components of the apparatus; one or more controllers for controlling behavior of one or more mechanized components of the apparatus; computer hardware and software for communicating with the one or more controllers, e.g., to initiate, pause, continue and/or repeat one or more operations performed by the apparatus; a power source for providing electrical power to the controller and any machinery of the device; an apparatus access system, such as one or more doors or locks, for providing selective access to one or more components or areas of the apparatus; a toilet seat above the toilet bowl; and/or an openable, closeable, and/or lockable and unlockable lid for providing selective access/access denial to the toilet bowl by a patient.

In an example method of using a biomaterial collection apparatus according to the present disclosure in order to collect a urine sample from each of at least a first and a second patient, the method can include the following steps. At least some of the steps are automated and controlled by a controller in response to one or more commands entered by an operator of the apparatus, such as a medical or law enforcement professional. The method steps include one or more of:

unlocking, e.g., by the operator, of the apparatus lid and opening the lid to expose the toilet bowl and initiate the sample collection process;

removing the plug from the collection port in the toilet bowl;

transporting, with a conveyance system, an unused collection cartridge from a cartridge dispenser into position below the collection port;

engaging a pneumatic device with the air intakes of the cartridge and/or with the conveyance system;

inflating the collection conduit and the collection vessel with the pneumatic device;

capturing an initial volume of urine from the first patient in the collection vessel via the collection conduit;

detecting that the initial volume of urine has been captured in the collection vessel;

sealing off the initial volume of urine in a first portion of the collection vessel to segregate the initial volume of urine from the remainder of the collection vessel;

subsequent to the sealing, capturing a second volume of urine from the first patient in the collection vessel;

detecting that the second volume of urine has been captured in the collection vessel;

sealing off the second volume of urine in a second portion of the collection vessel to segregate the second volume of urine from the first volume of urine and the remainder of the collection vessel;

capturing a third volume of urine from the first patient in the collection vessel subsequent to the capturing of the second volume of urine;

detecting that the third volume of urine has been captured in the collection vessel;

sealing off of the third volume of urine in a third portion of the collection vessel to segregate the third volume of urine from the first and second volumes of urine;

detaching the first, second, and third portions of the collection vessel from the remaining collection vessel;

detaching at least a portion of the collection conduit from the cartridge;

disposing the collection conduit, e.g., by flushing it via the first port of the toilet bowl;

closing and locking the lid;

unlocking and opening (e.g., by an operator) of a door on the apparatus to access and retrieve the sealed collection container portions and/or to retrieve a remaining portion of the used cartridge;

re-locking the door; and initiating collection of the second patient's urine by unlocking, e.g., by the operator, of the apparatus lid and opening the lid to expose the toilet bowl and initiate the sample collection process for the second patient as just described for the first patient.

According to another example method in accordance with the present disclosure, the method includes: detecting an initial volume of urine captured by a collection vessel, the initial volume being less than a total volume of urine captured by the vessel; sealing, in response to the detecting and before the total volume of urine is captured, the initial volume in a first portion of the vessel; and capturing, subsequent to the sealing, a first non-initial volume of urine in a second portion of the vessel.

In some examples, the method further includes sealing, subsequent to the capturing, of the first non-initial volume of urine in the second portion of the vessel.

In some examples, the method further includes capturing, subsequent to the sealing of the second portion of the vessel, a second non-initial volume of urine in a third portion of the vessel; and sealing, subsequent to the capturing of the second non-initial volume of urine, of the second non-initial volume of urine in the third portion of the vessel, wherein the total volume of urine is equivalent to a sum of the initial volume, the first non-initial volume, and the second non-initial volume.

In some examples, the sealing of the initial volume of urine is performed by a first pair of sealing arms that releasably press and seal the collection vessel at a first location on the vessel; the sealing of the first non-initial volume of urine is performed by a second pair of sealing arms that releasably press and seal the collection vessel at a second location on the vessel; and the sealing of the second non-initial volume of urine is performed by a third pair of sealing arms that releaseably press and seal the collection vessel at a third location on the vessel. Any number of pairs of sealing arms can be provided on a sealing apparatus to provide for a desired number of discretely sealed portions of a urine sample captured from a patient or subject, e.g., two, three four, five, six or more pairs of sealing arms.

In some examples, each of the sealings is controlled by a controller configured to activate the pairs of sealing arms in chronological sequence.

In some examples, each of the first, second and third pairs of sealing arms includes a heating element and a compressible pad.

In some examples, each of the first, second, and third pairs of sealing arms is activated by a solenoid.

In some examples, for each of the pairs of the sealing arms, one of the sealing arms is coupled to an extension shaft that extends from, and retracts towards, a plate to which the sealing arm is coupled.

In still further examples of the method in accordance with the present disclosure, the detecting is performed by one or more of a light/laser sensor, a heat sensor, a weight sensor, or a volume sensor.

A variety of additional aspects will be set forth in the description that follows. The aspects relate to individual features and to combinations of features. It is to be understood that both the foregoing general description and the following detailed description are exemplary and explanatory only and are not restrictive of the broad inventive concepts upon which the embodiments disclosed herein are based.

BRIEF DESCRIPTION OF THE FIGURES

The following drawings are illustrative of particular embodiments of the present disclosure and therefore do not limit the scope of the present disclosure. The drawings are not to scale and are intended for use in conjunction with the explanations in the following detailed description. Embodiments of the present disclosure will hereinafter be described in conjunction with the appended drawings, wherein like numerals denote like elements.

FIG. 5 is a top view of the biomaterial collection apparatus of FIG. 1.

FIG. 6 is a cross-sectional view of the biomaterial collection apparatus of FIG. 1 along the line 6-6 in FIG. 5, the apparatus being in a plugged mode.

FIG. 7 is a cross-sectional view of the biomaterial collection apparatus of FIG. 1 along the line 7-7 in FIG. 5, the apparatus being in a plugged mode.

FIG. 21A is an exploded view of the cartridge of FIG. 18.

DETAILED DESCRIPTION

Figure 1:
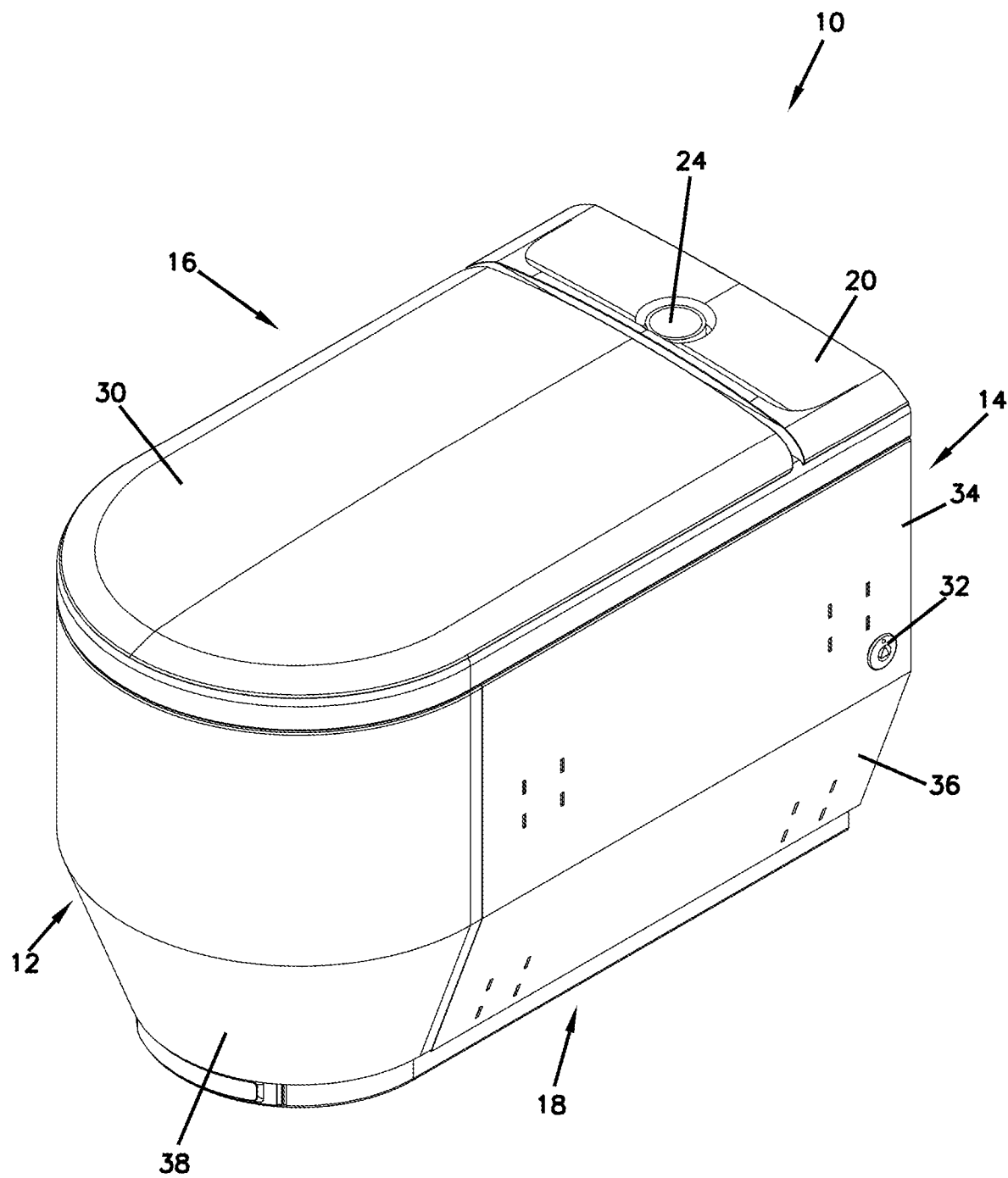
FIG. 1 is a front perspective view of a biomaterial collection apparatus in accordance with the present disclosure, the apparatus having a closed lid.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

As used throughout this disclosure, biomaterials include any biological substance produced by humans. Non-limiting examples of biomaterials include blood, urine, saliva, semen, feces, sweat, and so forth. The biomaterial collection system embodiments of the present disclosure will be described with particular reference to the collection of urine from a human subject or generic reference to the collection of biomaterial. It should be appreciated that principles of the embodiments described herein may be readily applied to the collection of biomaterials other than urine and other than from human subjects.

Referring to FIGS. 1-4, a biomaterial collection apparatus 10 generally includes a front 12, a back 14, a top 16 and a bottom 18. A tank 20 can hold water or other fluid that can be piped into a toilet bowl 22. A flusher 24 can be activated to flush contents of the toilet bowl into a sewage system via the sewage port 26 towards the rear of the toilet bowl 22. The sewage port 26 connects to a drainpipe 27.

Figure 2:
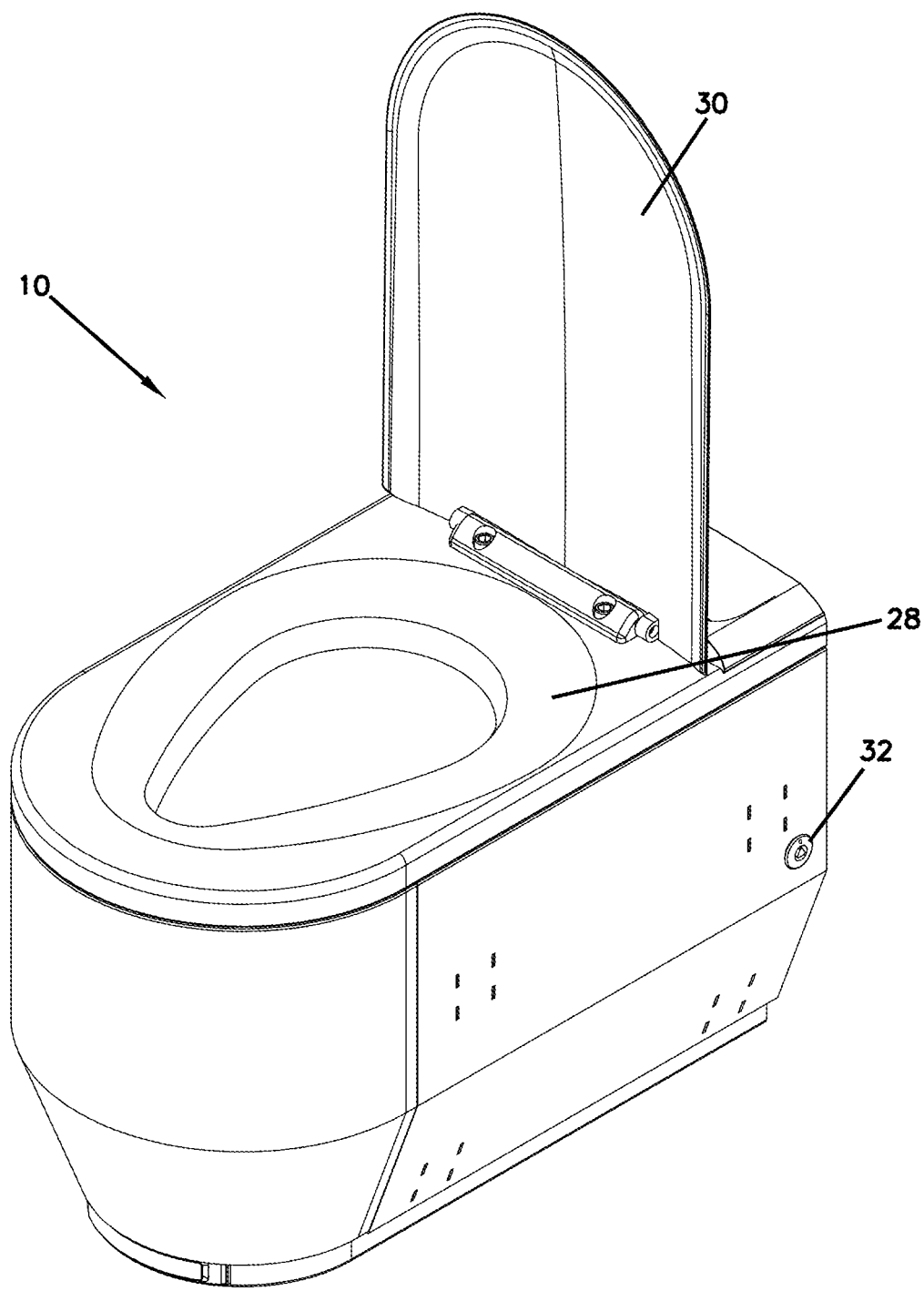
FIG. 2 is a front perspective view of the biomaterial collection apparatus of FIG. 1, the apparatus having an open lid.
Figure 3:
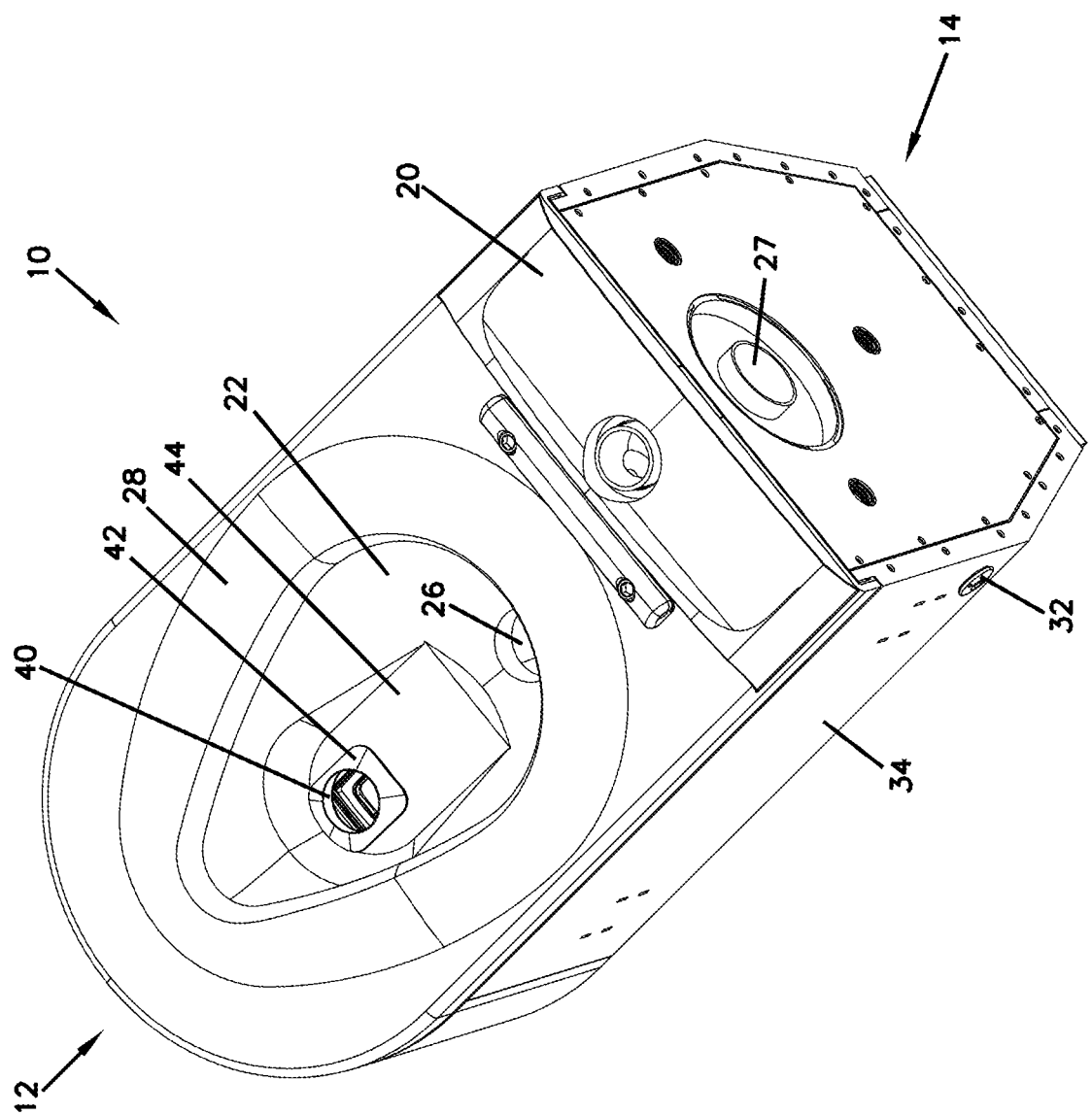
FIG. 3 is a rear, perspective view of the biomaterial collection apparatus of FIG. 1 shown without a lid.
Figure 4:
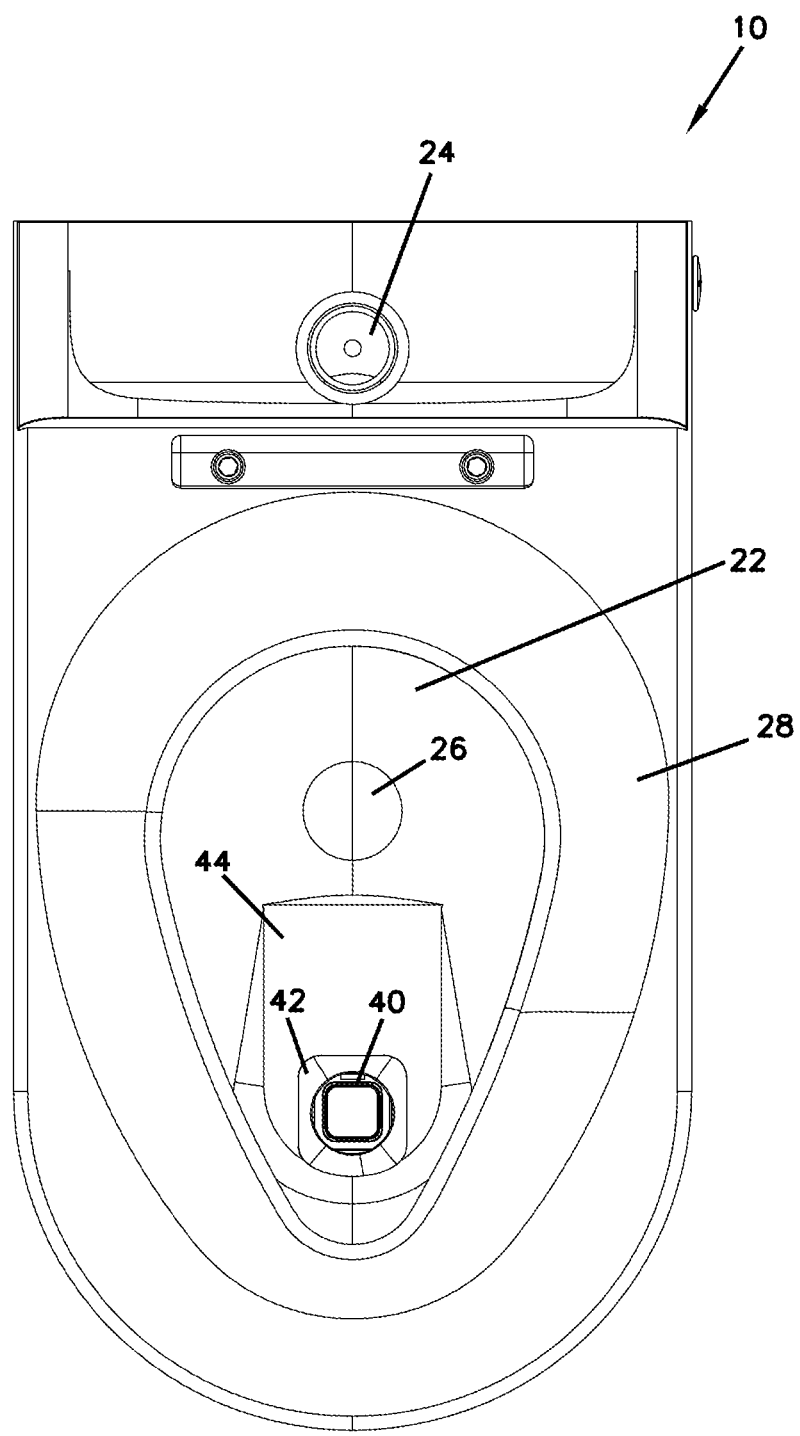
FIG. 4 is a top view of the biomaterial collection apparatus of FIG. 1 shown without a lid.
Figure 8:
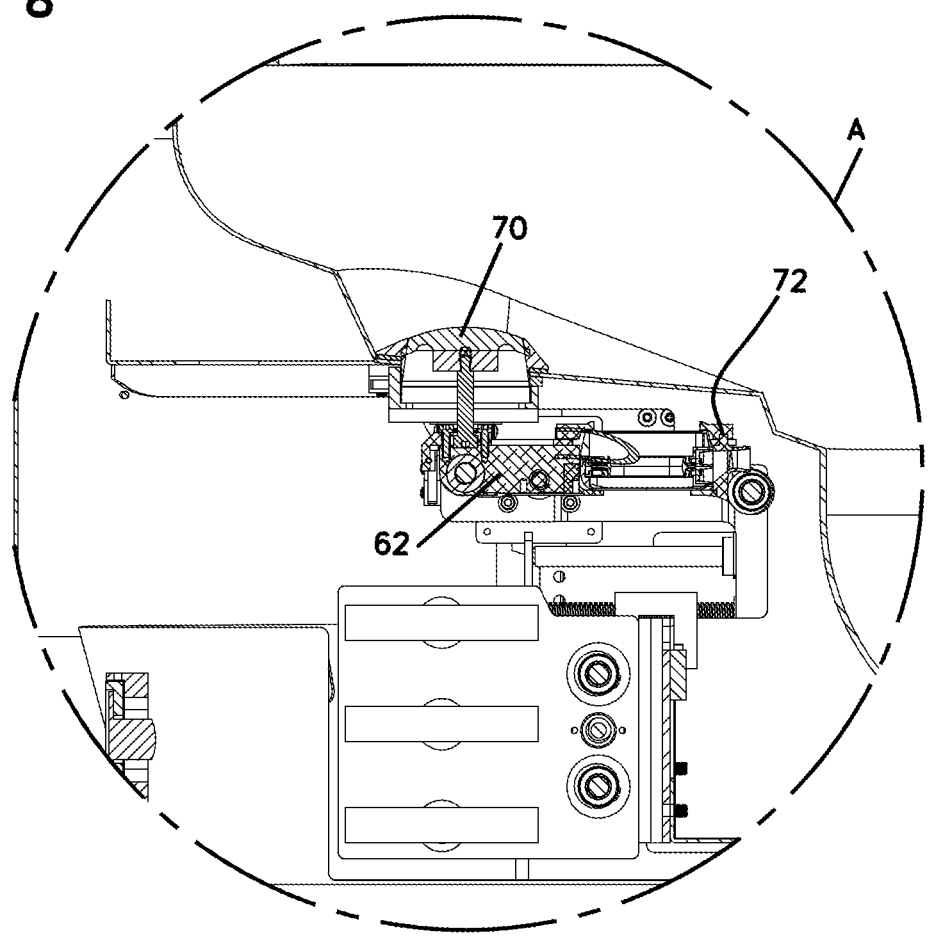
FIG. 8 is an enlarged view of the callout area A of FIG. 7.
Figure 9:
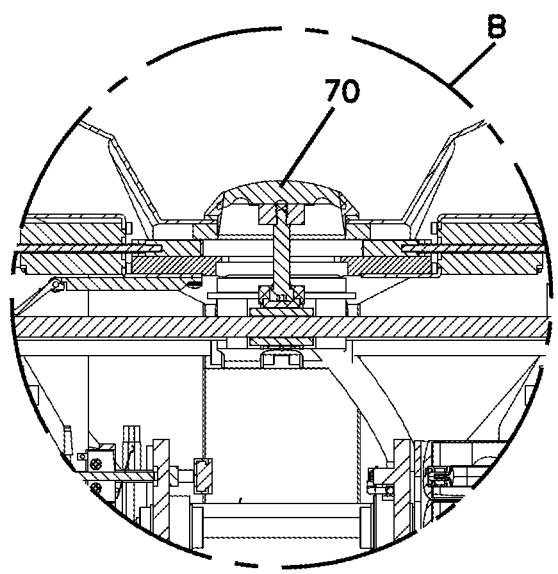
FIG. 9 is an enlarged view of the callout area B of FIG. 6.
Figure 10:
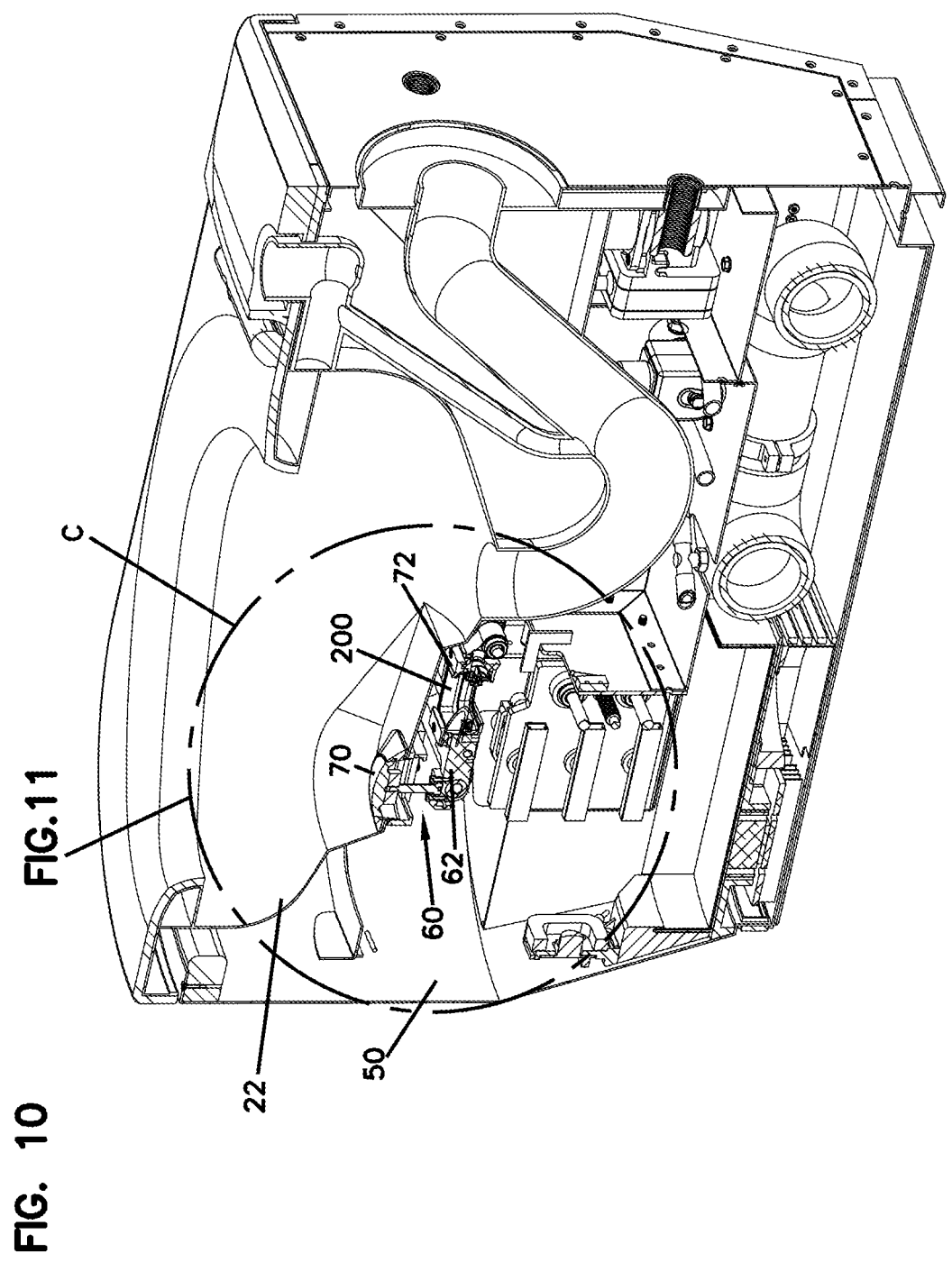
FIG. 10 is a perspective cross-sectional view along the line A-A in FIG. 5, the apparatus being in a plugged mode.
Figure 11:
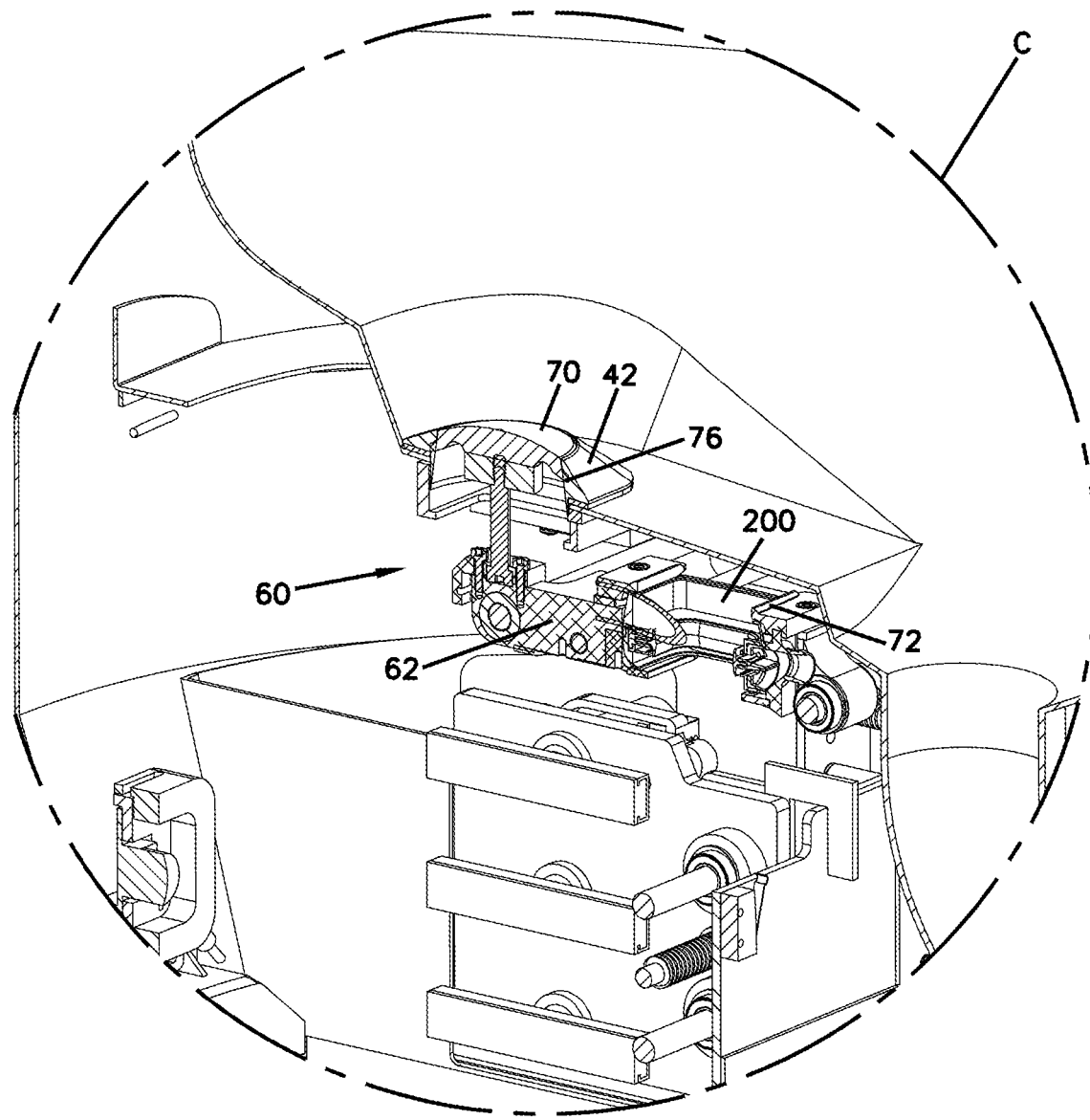
FIG. 11 is an enlarged view of the callout area C of FIG. 10.
Figure 12:
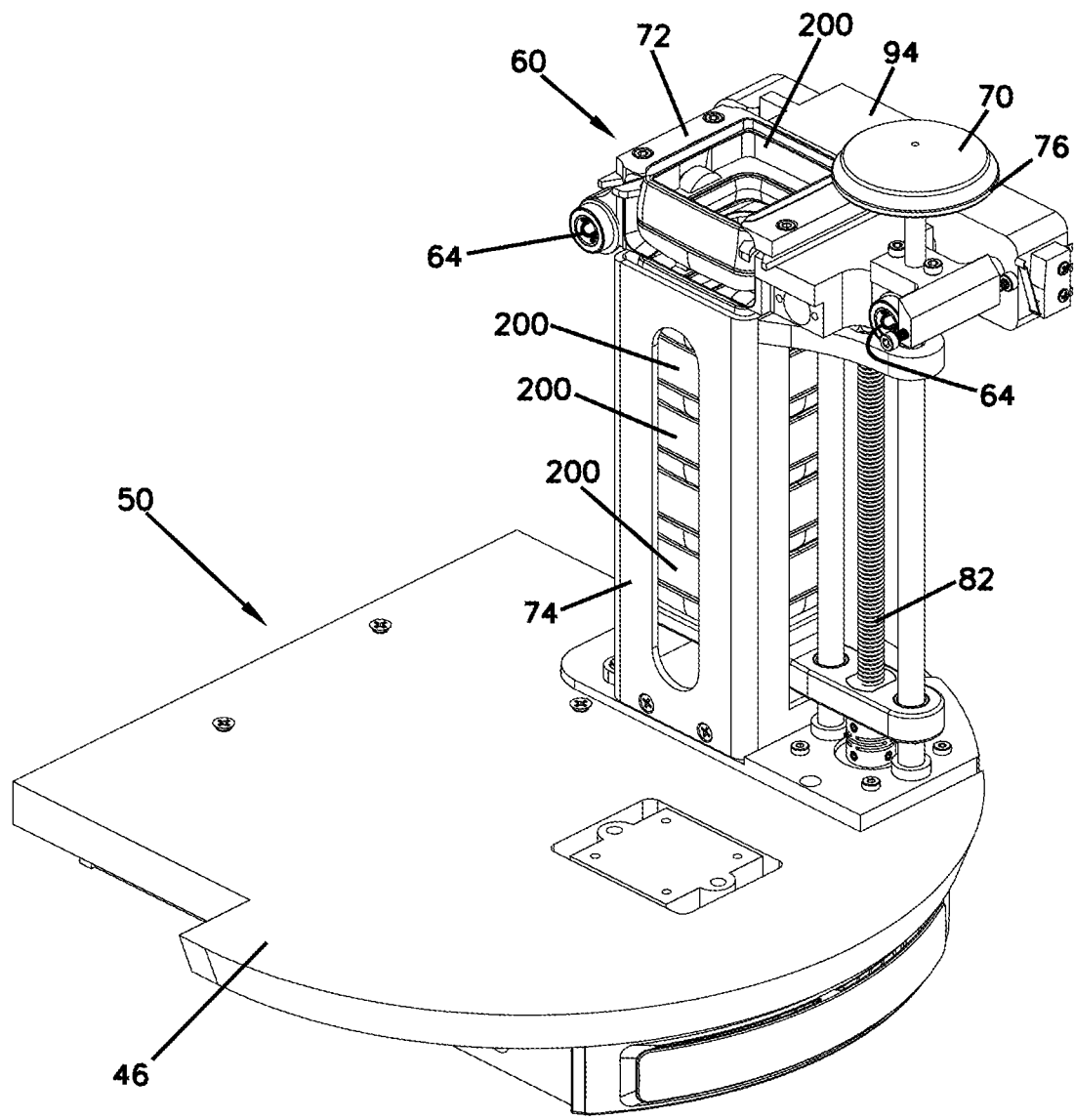
FIG. 12 is a perspective view of a cartridge collection assembly portion of the biomaterial collection apparatus of FIG. 1, including unused cartridges.
Figure 13:
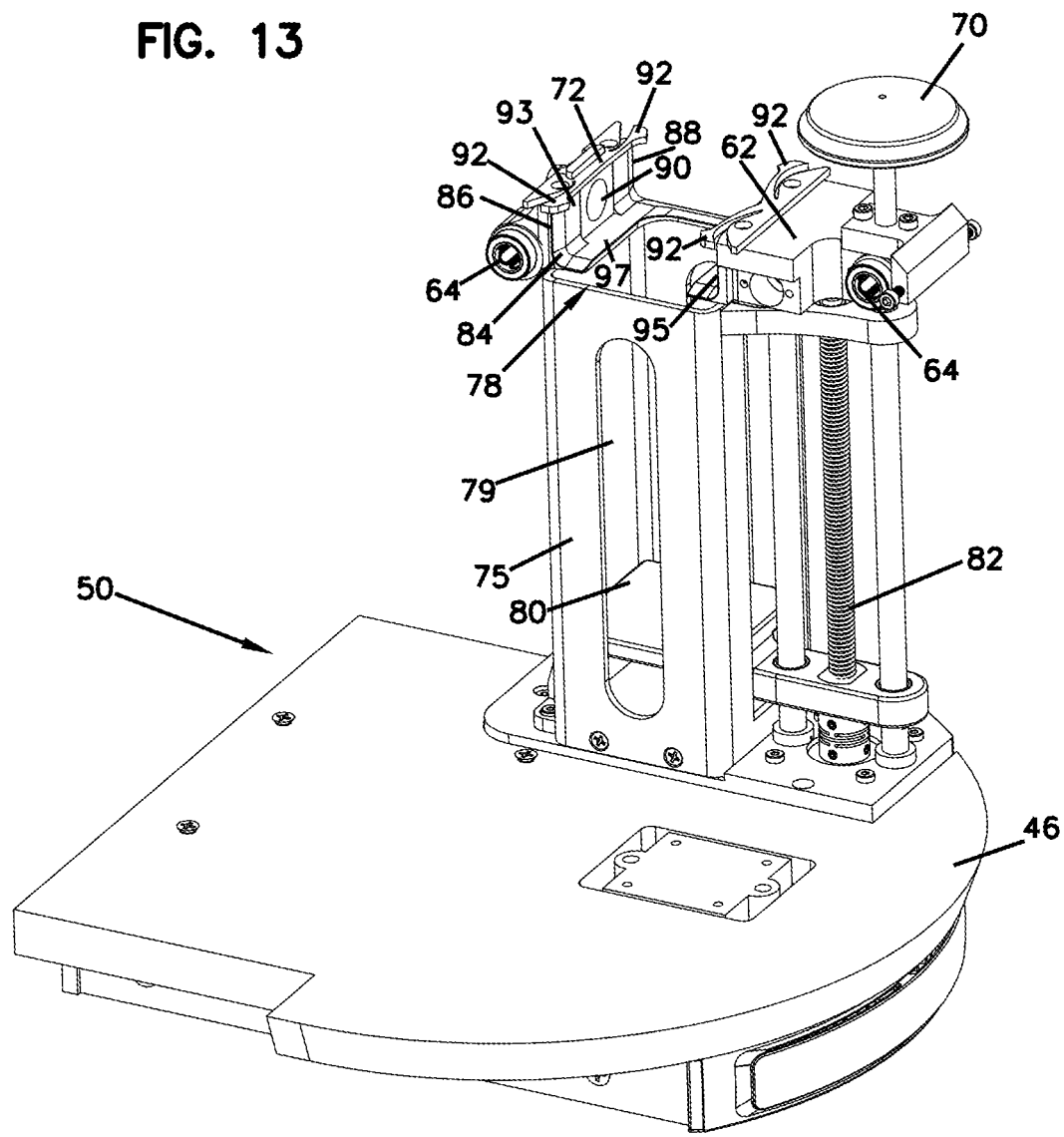
FIG. 13 is a perspective view of a portion of the cartridge collection assembly of FIG. 12, with all cartridges removed.
Figure 14:
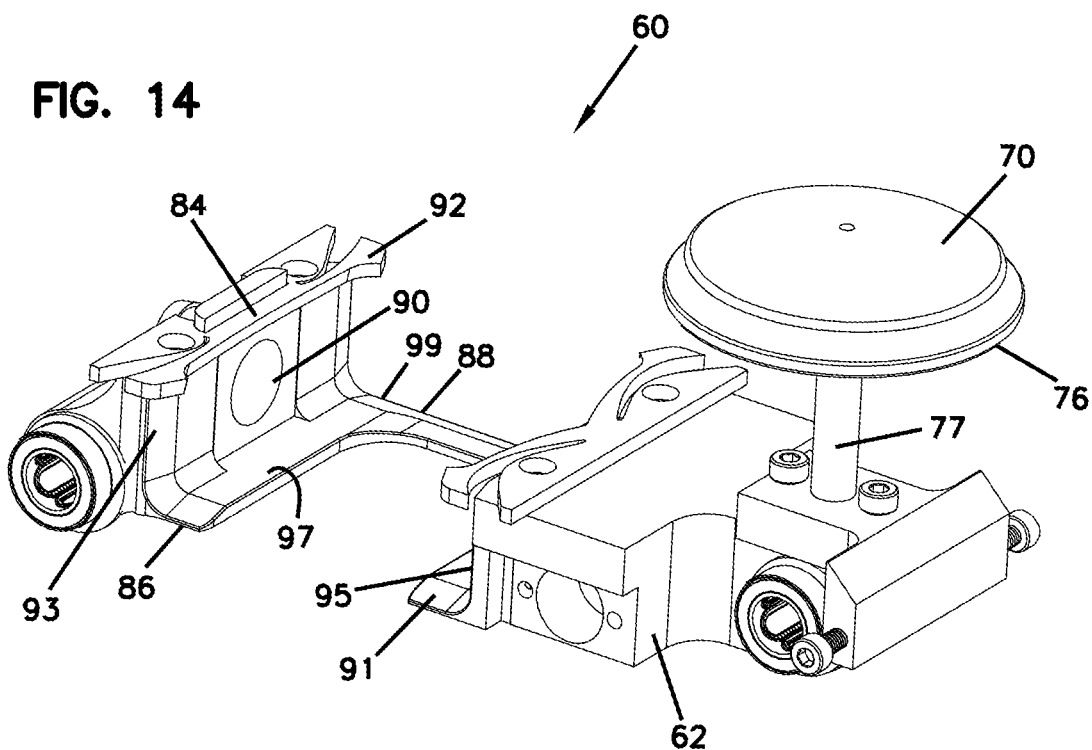
FIG. 14 is a perspective view of an example conveyance assembly of the apparatus of FIG. 1.
Figure 15:
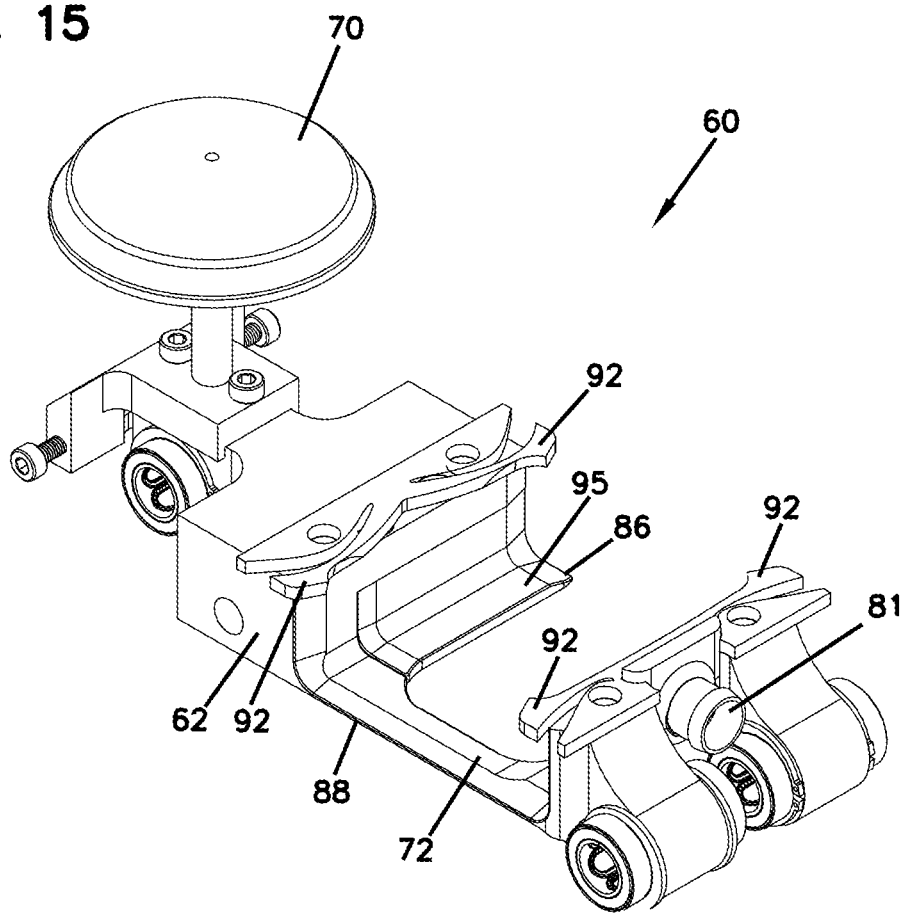
FIG. 15 is a further perspective view of the conveyance assembly of FIG. 14.

A toilet seat 28 surrounds the toilet bowl 22 above the toilet bowl 22. An openable and closable lid 30 can be selectively locked in the closed configuration shown in FIG. 1 and unlocked in order to open the lid as shown in FIG. 2. In the closed configuration, the lid 30 closes off the toilet bowl 22, which can minimize unauthorized access to the biomaterial collection components of the apparatus.

A key operated locking mechanism 32 can be used to lock and unlock the lid 30 and also to lock and unlock the access points to the sample processing area of the apparatus. These access points can include, e.g., one or more removable panels 34, 36, and a drawer 38 that can be pulled out (towards the front 12) and pushed back in along drawer tracks.

A second port or sample collection port 40 is disposed towards a front of the toilet bowl 22. The collection port 40 can be openable and closeable with a plug. To facilitate a liquid tight seal when plugged, the collection port 40 can optionally be surrounded by a gasket 42 or other sealing element adapted to provide a liquid tight seal when abutting the plug with sufficient contact force. The example collection port 40 defines a substantially round opening adapted to receive a substantially round plug head, although other shapes and configurations may also be used. Optionally, the collection port 40 is disposed on a substantially planar surface 44 of the toilet bowl 22 that is pitched downward (i.e., toward the Earth) toward the sewage port 26 disposed rearward of the collection port 40. The planarity of the surface 44 can facilitate sealing of the plug head and the collection port 40, and the downward pitch of the surface 44 can facilitate migration of uncollected biomaterials and waste components, from the collection system, such as the used, detached collection conduit, towards the sewage port 26 for flushing out of the apparatus 10.

The apparatus 10 can operate in a variety of modes including, e.g., a plugged mode, a collection mode, a retrieval mode, and various transitional modes in which the apparatus transitions between two operating modes.

In the plugged mode the collection port is plugged and the apparatus 10 can operate as an ordinary toilet and/or be locked to prevent access to the apparatus by a non-operator. In the collection mode, the collection port is unplugged, and the cartridge is vertically aligned with the collection port with a collection conduit and collection vessel deployed from the cartridge. In a retrieval mode, the collection port can be plugged or unplugged, the cover can be locked to prevent access to the toilet bowl, the collected sample or samples are sealed and retrievable from the apparatus, and the used remainder of the cartridge is retrievable from the apparatus.

Referring now to FIGS. 6-11, the apparatus 10 is depicted in a plugged mode. The apparatus includes a sample processing volume 50 below the toilet bowl 22. The processing volume 50 houses various components and systems of the apparatus. Access to the sample processing volume 50 can be regulated with the locking mechanism 32, the panels, 34, 36, and the drawer 38.

Examples of components and systems that the processing volume 50 can house include: guide tracks for the drawer 38, a cartridge dispenser holding one or more unused cartridges, a conveyance assembly 60, a pneumatic system 600, a vessel sealing system 500, heating or refrigeration systems, visual or other sensors, one or more electronic controllers, and/or a receptacle 100 for discarded used cartridges.

Figure 16:
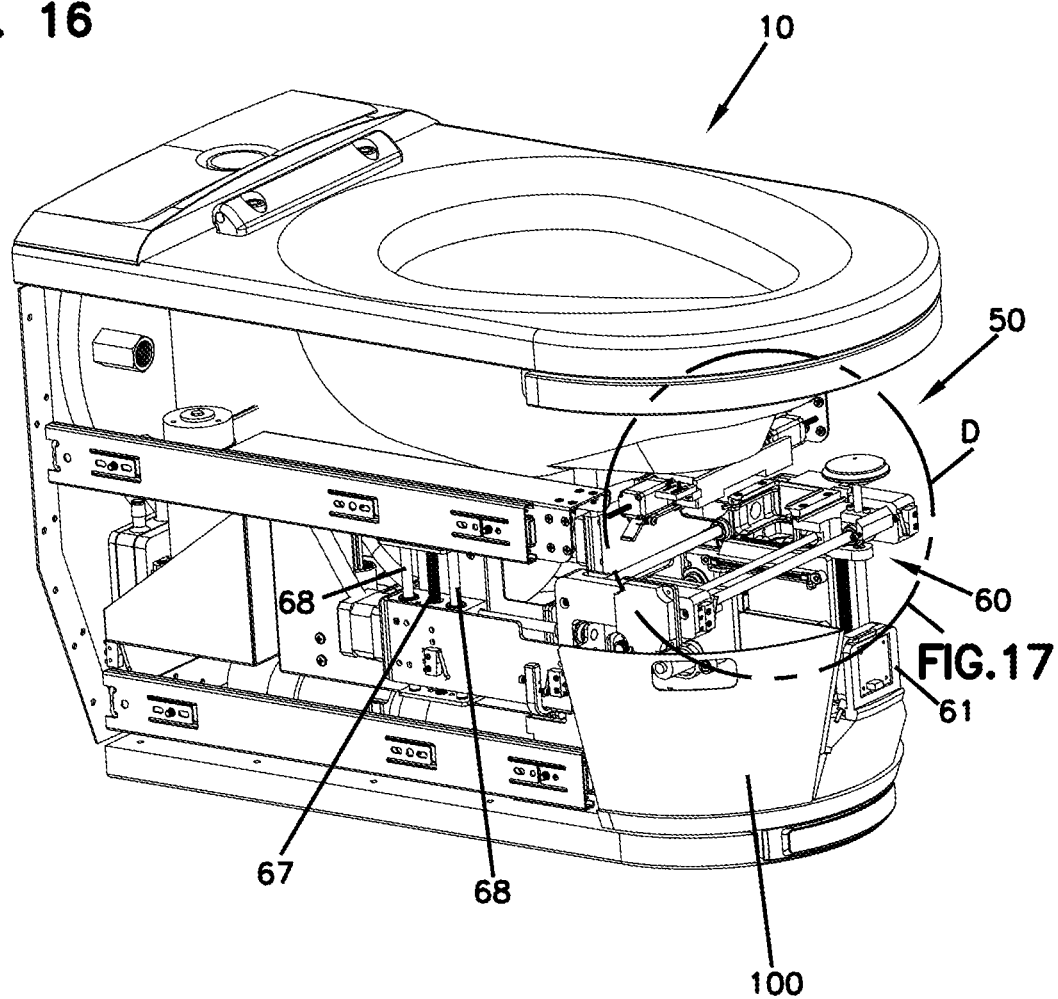
FIG. 16 is a perspective view of a portion of the interior of the apparatus of FIG. 1 showing the positioning of the cartridge collection assembly of FIG. 12.
Figure 17:
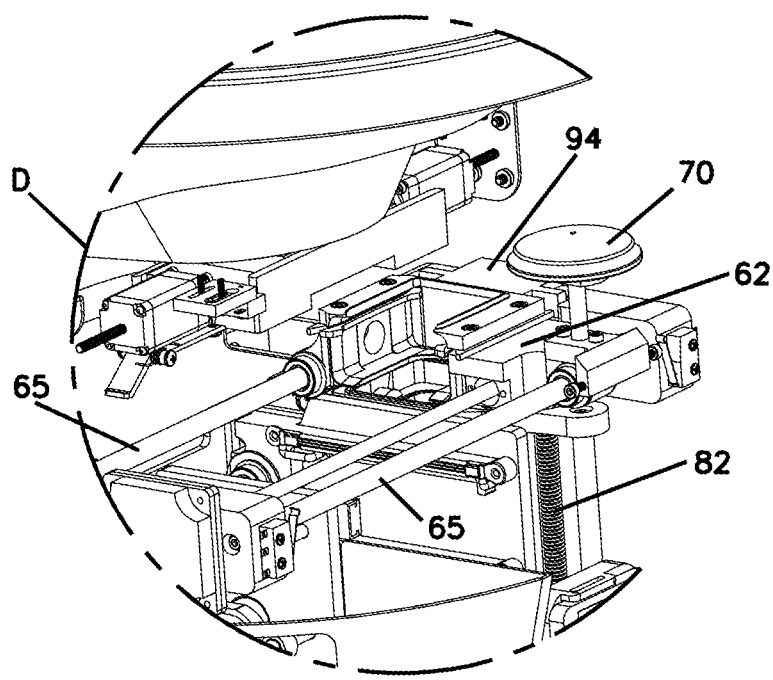
FIG. 17 is an enlarged view of the callout area D of FIG. 16.
Figure 18:
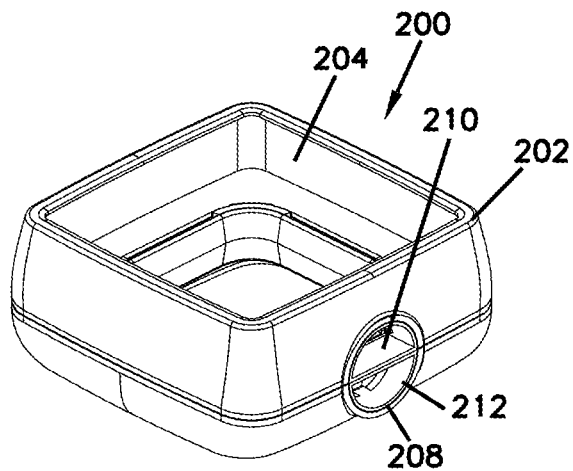
FIG. 18 is a top perspective view of an example collection cartridge used with the apparatus of FIG. 1.
Figure 19:
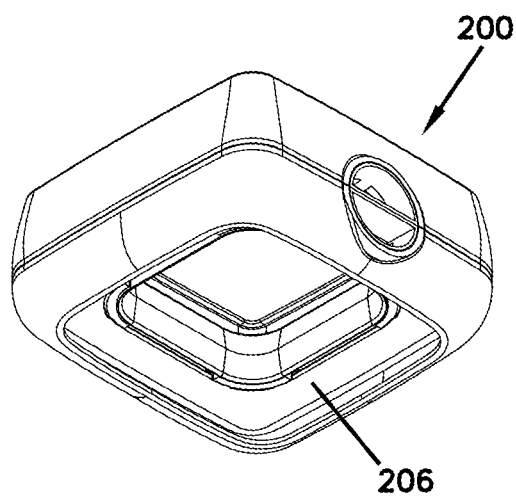
FIG. 19 is a bottom perspective view of the cartridge of FIG. 18.
Figure 20:
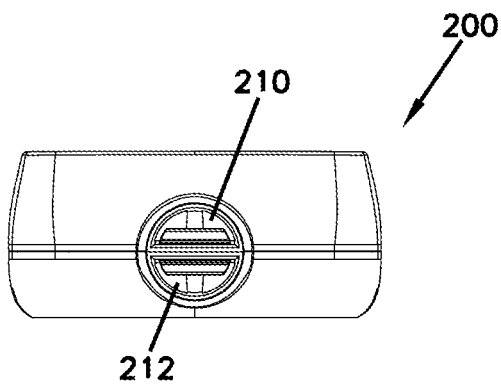
FIG. 20 is a rear view of the cartridge of FIG. 18.

Referring now to FIGS. 12-17, the conveyance assembly 60 includes a main body 62 that is coupled to both the plug 70 and a cartridge basket 72. The main body 62 is controlled by a controller and moveable in three dimensions through a series of linear drives. Thus, the conveyance system is adapted to move the plug 70 and a cartridge basket 72 between various positions dictated by the translational limits of the drives. The cartridge basket 72 and plug 70 can be moved independently of each other, or in tandem. In some examples, the drives can include threaded rods or drive screws that convert rotational motion of the rod/screw into translational movement of the main body 62 parallel to the axis of the rod/screw. One or more guides, such as the guides 64 can receive corresponding guide rods 65 that support the conveyance assembly 60 during translational motions. Referring to FIG. 16, up and down translational movement of the conveyance assembly 60 can be provided by, e.g., the drive screw 67 and vertical guides 68.

In a first motion, the conveyance assembly 60 lowers the plug 70 out of the collection port 40 and into the sample processing volume 50.

In a second motion, the conveyance assembly 60 can move the lowered plug horizontally such that it is no longer vertically aligned with the collection port 40.

In a third motion (which can coincide with the second motion) the conveyance system moves the cartridge basket 72 to the cartridge dispenser 74 such that the basket 72 captures the uppermost unused cartridge 200 in the dispenser 74.

In a fourth motion the conveyance assembly 60 moves the captured cartridge 200 in the basket 72 into a position within the sample processing volume 50 that is below and vertically aligned with the collection port 40.

In an optional fifth motion, the conveyance assembly 60 can raise the captured cartridge 200 into position below the collection portion 40 such that the collection conduit, when inflated, will expand partially into the toilet bowl 22.

Following collection of a biomaterial sample, in a sixth motion the conveyance system can move the used portion of the cartridge 200 still held in the basket 72 to a position within the processing volume 50 where the basket can release the used cartridge into a waste receptacle, such as the receptacle 100, which is optionally removable from the processing volume 50 (and subsequently replaceable therein).

In a seventh motion the conveyance assembly 60 can move the plug 70 back into vertical alignment with the collection portion 40.

In an eighth motion, the conveyance assembly 60 can raise the plug 70 into the collection port 40 to seal off the collection port 40 prior to a subsequent biomaterial sample collection.

The plug 70 can include an annular rib 76 adapted to seal against the gasket 42. In some examples, the gasket 42 can include an annular groove adapted to receive the annular rib 76.

Referring now to FIGS. 12-15, a leg 77 extends from the main body 62 of the conveyance assembly 60 to support the plug 70 above the main body 62.

The cartridge dispenser 74 is secured to a base 46 that at least partially defines the bottom of the sample processing volume 50. The cartridge dispenser 74 includes a wall 75 that defines an interior volume 79 of the dispenser 74 that receives a stack of cartridges 200. The dispenser 74 has an open top 78. The uppermost cartridge 200 in the stack rests above the open top 78 and above the wall 75 so that it can be captured by the basket 72.

A movable horizontal platform 80 on which the lowermost cartridge 200 rests, can be moved up and down, e.g., via the motorized vertical drive screw 82 that is coupled to the platform 80. Thus, as each cartridge is used, the platform 80 can be incrementally raised to enable capture of the next cartridge in the stack. In addition, the platform 80 can be lowered so that the dispenser 74 can receive additional fresh cartridges. A controller can be used to control the positioning of the platform 80.

The cartridge basket 72 includes a frame 84 having substantially open opposing sides 86 and 88, as well as a substantially open top and bottom. A rear wall 93 of the basket includes an aperture 90 adapted to align with the air intake on the cartridge 200. The rear wall 93 engages the nozzle of the pneumatic hose when the hose is connected for purposes of inflating the collection conduit and collection vessel of the cartridge 200. The captured cartridge rests on the base 97 of the basket 72 and is retained by flexible retaining members 92 adapted to, e.g., resiliently snap around the outer shell of the cartridge 200.

To load a cartridge in the basket 72, the empty basket moves over to the dispenser 74 and the uppermost cartridge slides into the frame 84 starting from the side 88 towards the side 86. A stop block 94 can prevent the basket 72 from pushing the cartridge 200 off the stack of cartridges during the loading process. Once loaded, the flexible retaining members 92 hold the cartridge in proper alignment within the basket 72, such that the air inlet 81 on the rear wall 93 of the basket 72 is aligned with the air inlet of the cartridge and in communication with each other via the aperture 90.

With the cartridge 200 loaded in the basket 72, the basket can move into position for urine collection, wherein deployment of the collection conduit and collection vessel can take place. Following collection, the basket 72 containing the discardable components of the cartridge 200 moves to another area of the processing volume 50 where those discardable components are released from the basket 72, e.g., by snagging the cartridge shell with snagging a element, such as a hook, and moving the basket away while the shell is snagged. One or more beveled edges 91, 99 can facilitate loading and unloading of the cartridge 200.

The cartridge basket 72 can include a sensor/detector, such as an electronic weight sensor or scale 95 that detects weight changes of the cartridge 200, e.g., as the vessel of the cartridge fills with urine. For example, as the vessel fills with urine the amount of weight detected by the sensor 95 will increase. As the weight increases during urine capture and predefined weight thresholds are detected by the sensor 95, signals can be sent between the cartridge basket 72 and the vessel sealing system 500 to trigger activation of the appropriate pair of sealing arms of the sealing system 500 sequentially (from the bottom up) as higher and higher weight thresholds are detected.

Referring now to FIGS. 18-23, the cartridge 200 includes a housing 202 defining first and second chambers 204 and 206. The first chamber 204 is adapted to house or substantially house an expandable and collapsible biomaterial sample collection conduit, such as a funnel, in its collapsed state. The second chamber 206 is adapted to house or substantially house an expandable and collapsible collection vessel, such as a bag, in its collapsed state.

In some examples, one or both of the collection conduit and the collection vessel is/are inflatable and the cartridge housing defines an air inlet 208 in communication with at least one of the collection conduit or the collection vessel. In these examples, each of the collection vessel and the collection conduit defines one or more inflatable bladders having an inflation opening.

In some examples, the cartridge housing 202 defines two air inlets 210 and 212, one inlet 212 being in communication with an interior of the bladder or bladders of the inflatable collection vessel via its inflation opening, and the other inlet 210 being in communication with an interior of the bladder or bladders of the inflatable collection conduit via its inflation opening.

The cartridge housing 202 can comprise a rigid shell made from, e.g., a rigid plastic. In some examples the rigid shell can include first and second shell pieces 214 and 216 that are couplable to each other, e.g., via a snap fit or frictional fit or, alternatively, with a coupling medium, such as an adhesive. The first shell piece 214 can define or partially define the first chamber 204 and the second shell piece 216 can define or partially define the second chamber 206.

In some examples, the cartridge includes an anchoring unit 220 disposed between the first and second shell pieces 214 and 216 and coupled to each of the shell pieces. The anchoring unit 220 is adapted to anchor each of the collection vessel and the collection conduit to the cartridge and to couple and hermetically seal the inflation opening of each to its corresponding air inlet on the cartridge.

The anchoring unit 220 includes a vessel manifold 222 and a conduit manifold 224. Structurally, the vessel manifold 222 and the conduit manifold 224 can be identical to each other.

Each of the vessel manifold 222 and the conduit manifold 225 includes first and second frame members 226, 228, and 230, 232 defining an air inlet 212, 210, respectively, and cooperating with each other to anchor, respectively, the collection vessel and the collection conduit with a hermetic or substantially hermetic seal formed between the air inlet 212, 210 and the inflation opening of the vessel and conduit, respectively.

In some examples, one of the first and second frame members 226, 228 and 230, 232 of each of the vessel manifold 222 and the conduit manifold 224 is adapted to securely couple to one of the shell pieces 216, 214, respectively.

In addition, the anchoring unit 220 can include a divider 234 that separates the vessel manifold 222 from the conduit manifold 224. The divider 234 includes a central opening 237 defined by a wall 239 surrounding the opening 237. When the collection vessel and the collection conduit are deployed from the cartridge 200, the bottom of the collection conduit is in open communication with a top of the collection vessel via the opening 237, such that urine passes through the collection conduit into the collection vessel via the opening 237.

According to certain examples, one of a flexible inner skin or flexible outer skin of the collection vessel on a first side of the vessel's inflation opening is securely pressed between the frame members 226 and 228, while the other of the inner skin or outer skin of the collection vessel on an opposing side of the vessel's inflation opening is securely pressed between the divider 234 and the frame member 226. The pressing can occur between opposing surfaces of adjacent components of the cartridge. In addition, the collection vessel skin can be adhered to such surfaces, such as the surfaces 227, 229 shown in FIGS. 21A and 21B (collectively, FIG. 21).

Figure 21B:
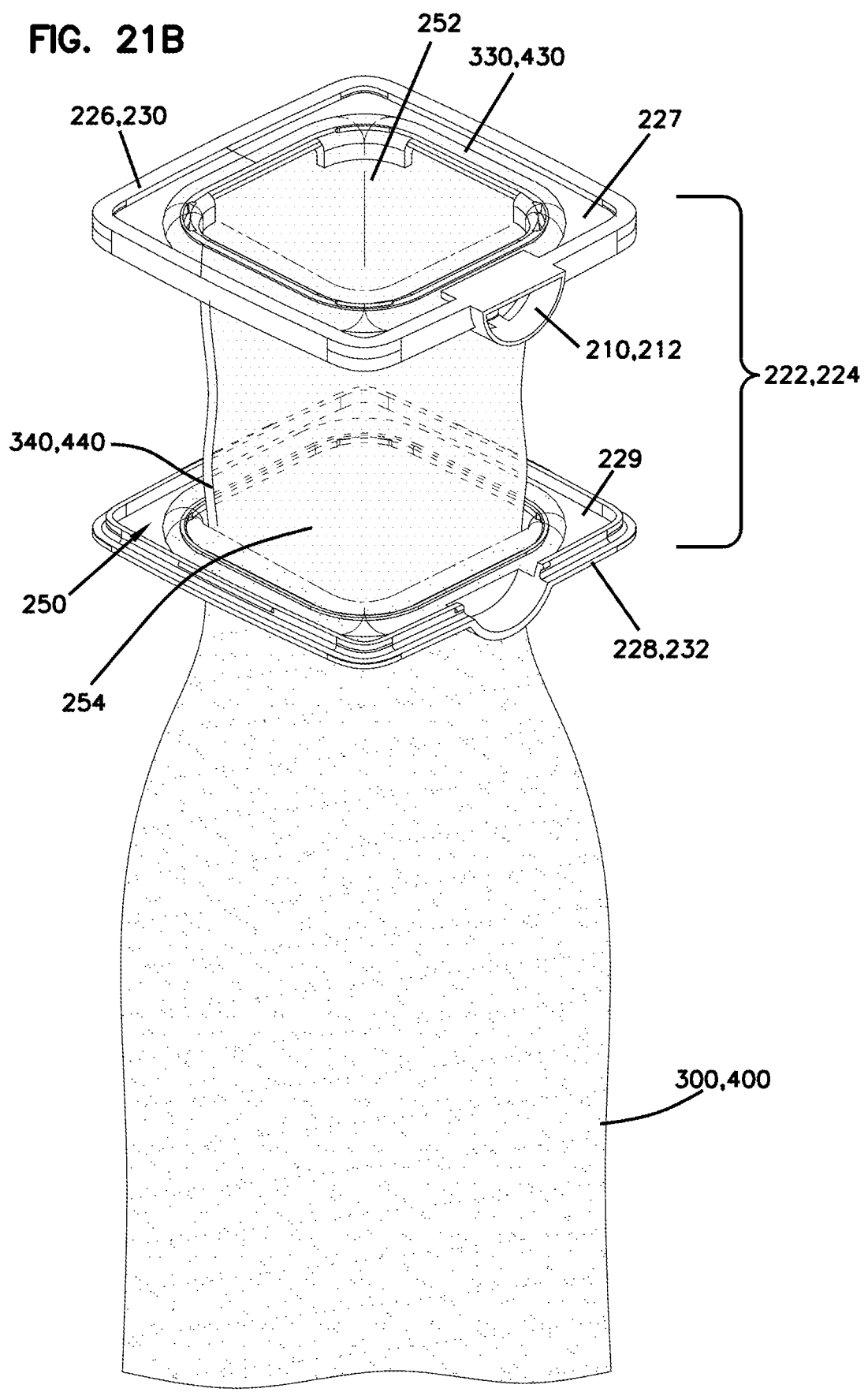
FIG. 21B is an exploded view of a manifold portion of the cartridge of FIG. 18, including a schematic vessel or conduit.
Figure 22:
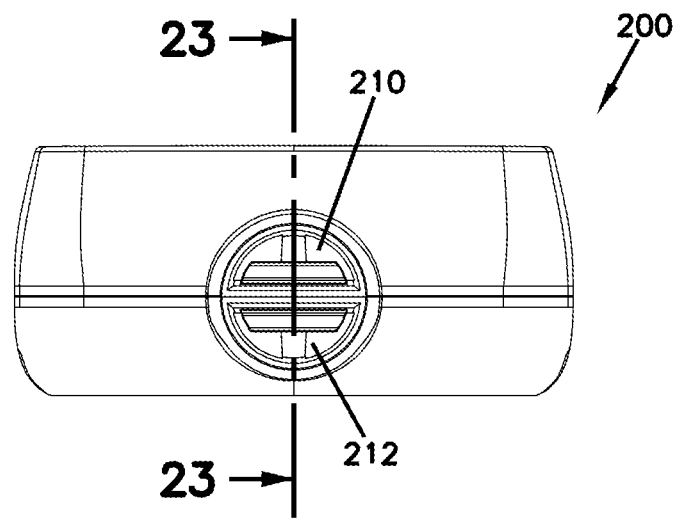
FIG. 22 is a rear view of the cartridge of FIG. 18.
Figure 23:
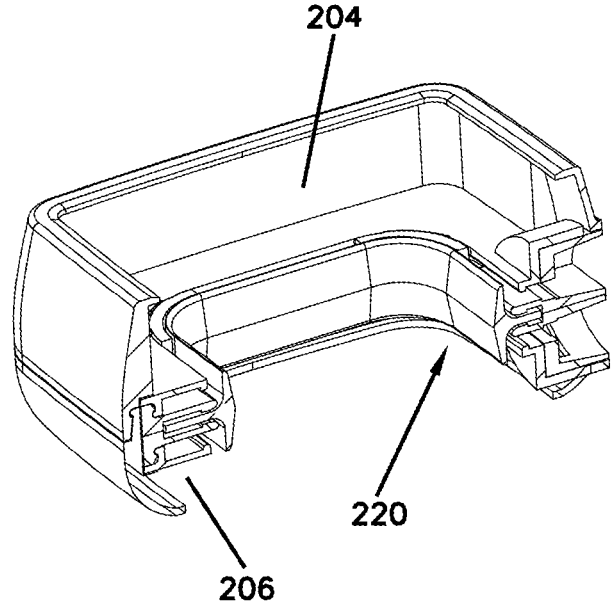
FIG. 23 is a cross-sectional view of the cartridge of FIG. 18 along the line 23-23 in FIG. 22.

Referring specifically to FIG. 21B, a manifold 222, 224 is shown in exploded view illustrating schematically an example fixation of a conduit 300 or vessel 400 to the manifold 222, 224. The inner skin 330, 430 of the conduit 300 or vessel 400, respectively, is adhered to the surface 227 around the entire perimeter of the aperture 252 of the frame member 226, 230. The outer skin 340, 440 of the conduit 300 or vessel 400, respectively, is adhered to the surface 229 around the entire perimeter of the aperture 254 of the frame member 228, 232.

When the frame member (226, 230) and the frame member (228, 232) are coupled to each other, an air channel 250 is formed between the inner skin 330, 430 and the outer skin 340, 440. The air channel 250 is in gaseous communication with the air inlet 210, 212 and approximately follows the perimeter of the apertures 252, 254, helping to direct air/gas passing into the channel 250 into the entirety of the bladder formed between the inner skin 330, 430, and the outer skin 340, 440 to thereby at least substantially uniformly inflate the conduit 300 or the vessel 400.

Figure 24:
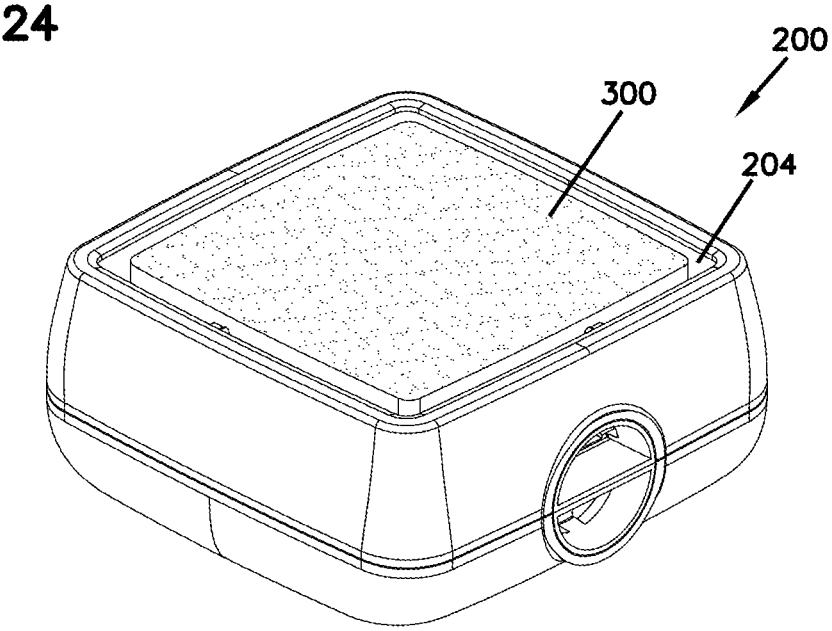
FIG. 24 is a top perspective view of the example collection cartridge of FIG. 18 with a schematically drawn uninflated collection conduit installed therein.
Figure 25:
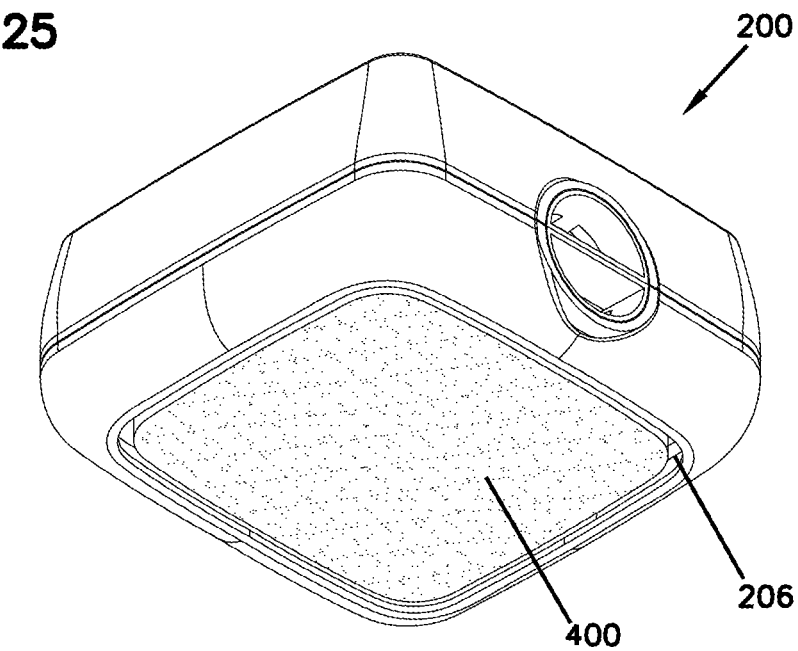
FIG. 25 is a bottom perspective view of the cartridge of FIG. 18 with a schematically drawn uninflated collection vessel installed therein.
Figure 26:
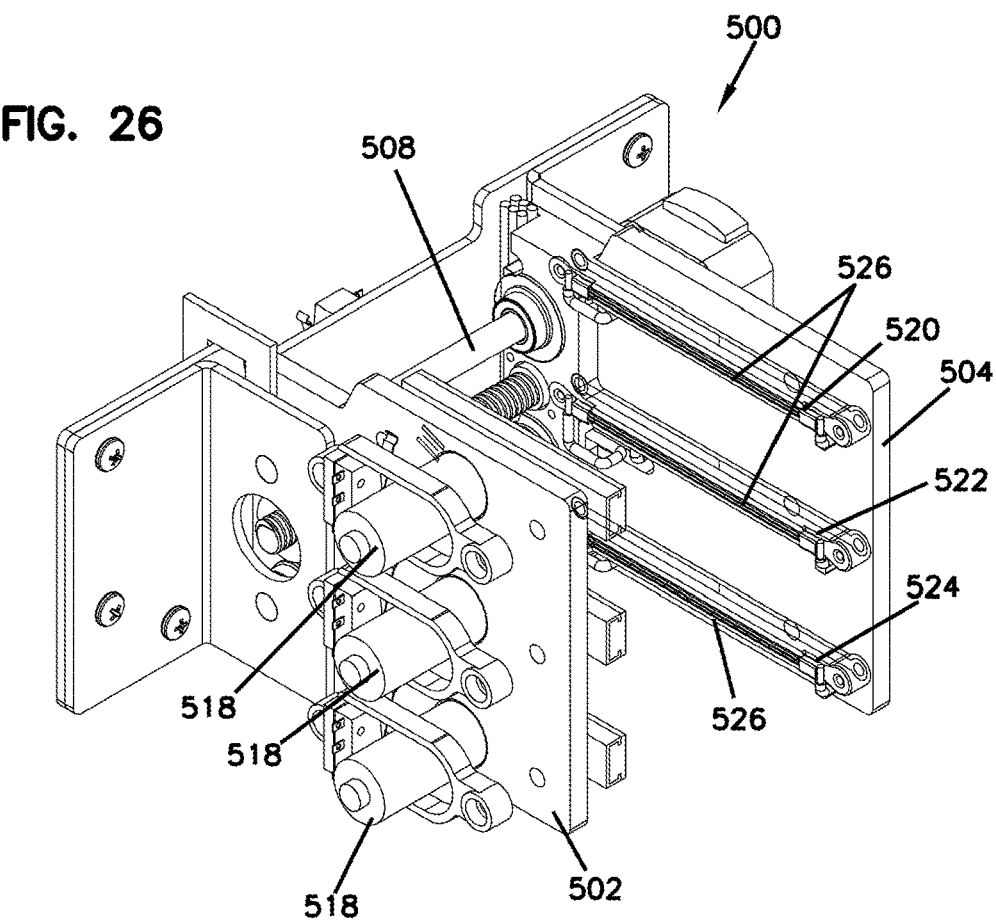
FIG. 26 is a top perspective view of an example vessel sealing assembly used with the apparatus of FIG. 1, the vessel sealing assembly being in a non-activated configuration.
Figure 27:
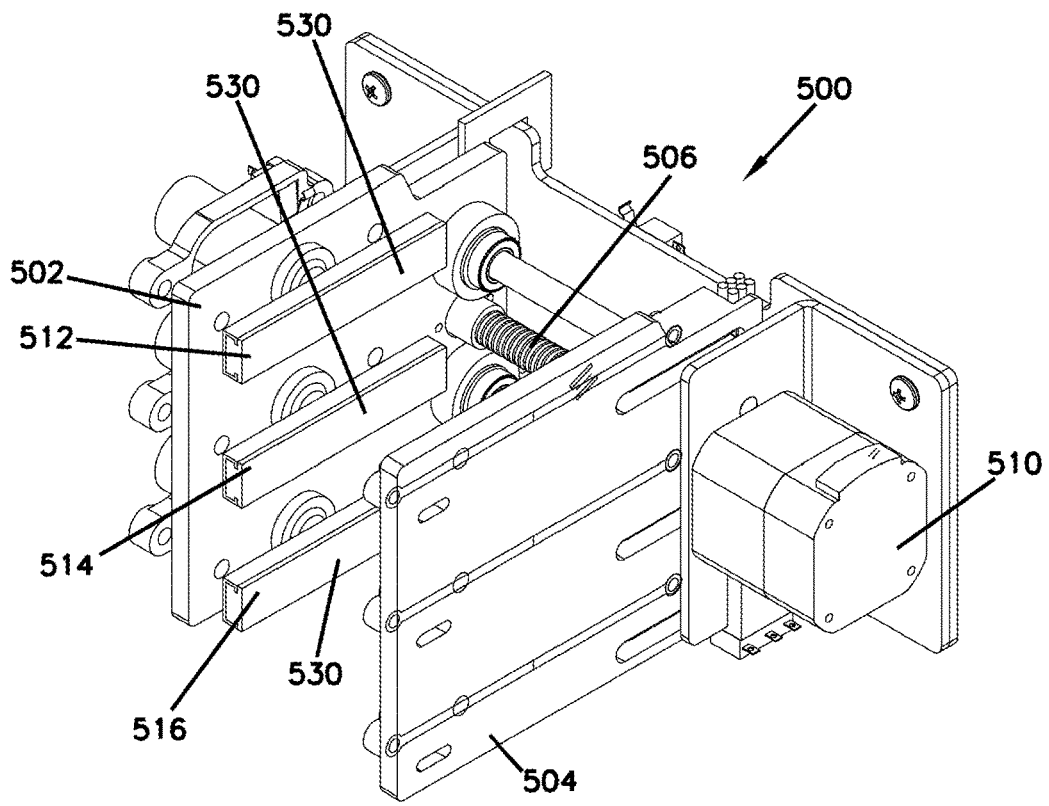
FIG. 27 is a further top perspective view of the vessel sealing assembly of FIG. 26.
Figure 28:
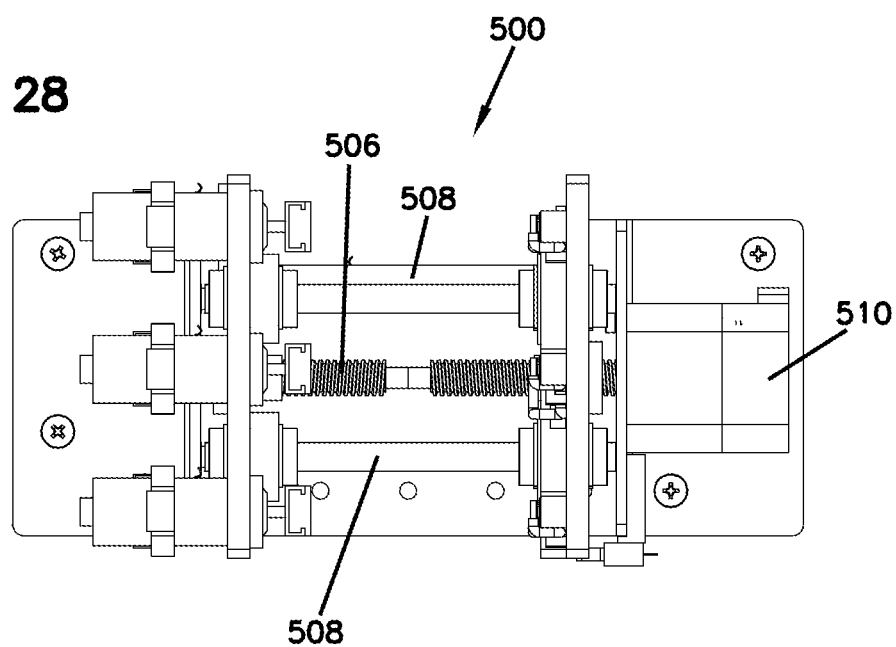
FIG. 28 is a front view of the vessel sealing assembly of FIG. 26.
Figure 29:
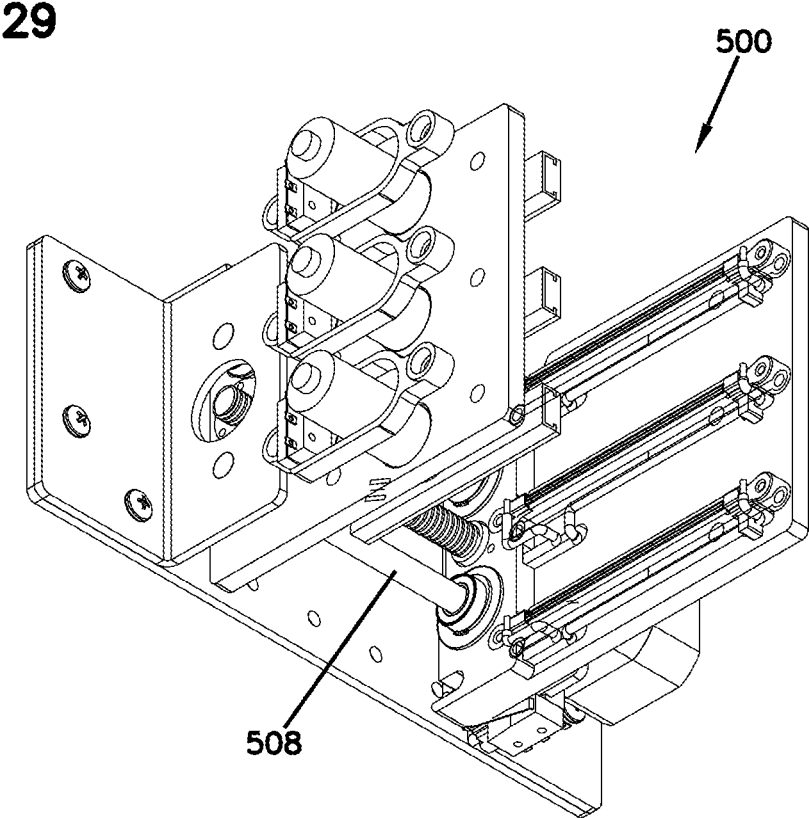
FIG. 29 is a bottom perspective view of the vessel sealing assembly of FIG. 26.
Figure 30:
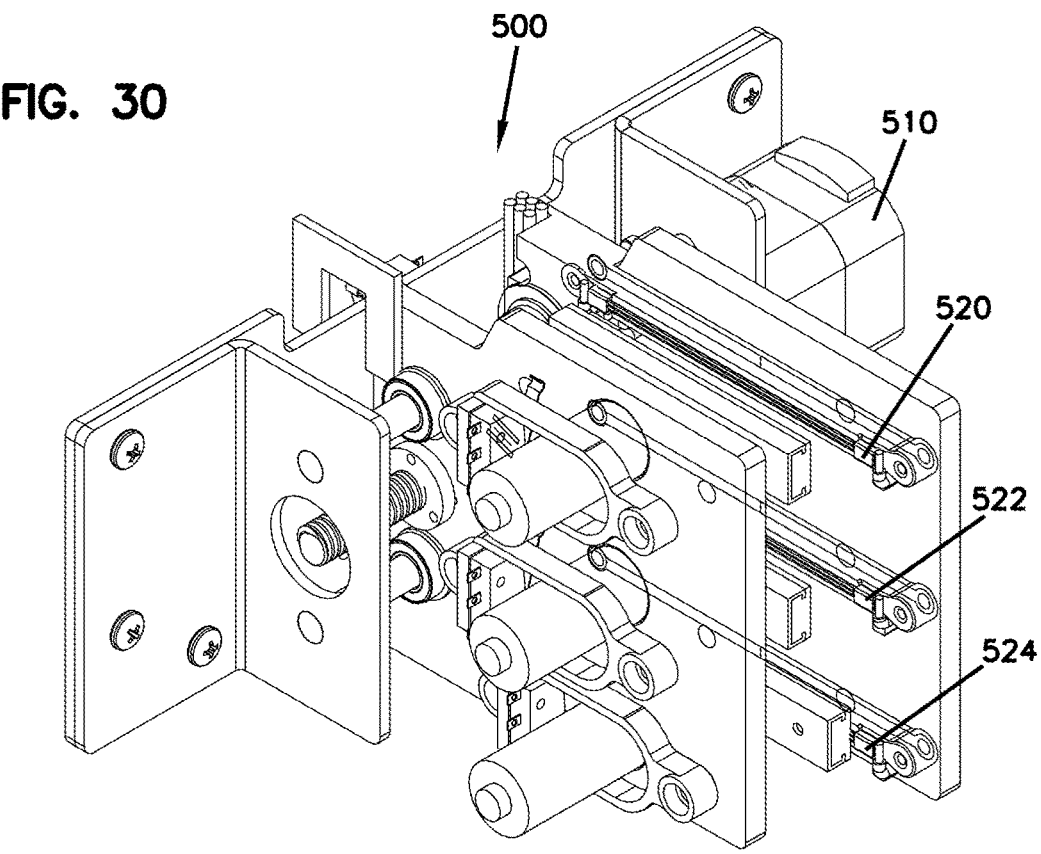
FIG. 30 is a top perspective view of the vessel sealing assembly of FIG. 26, the vessel sealing assembly being in a first activated configuration.
Figure 31:
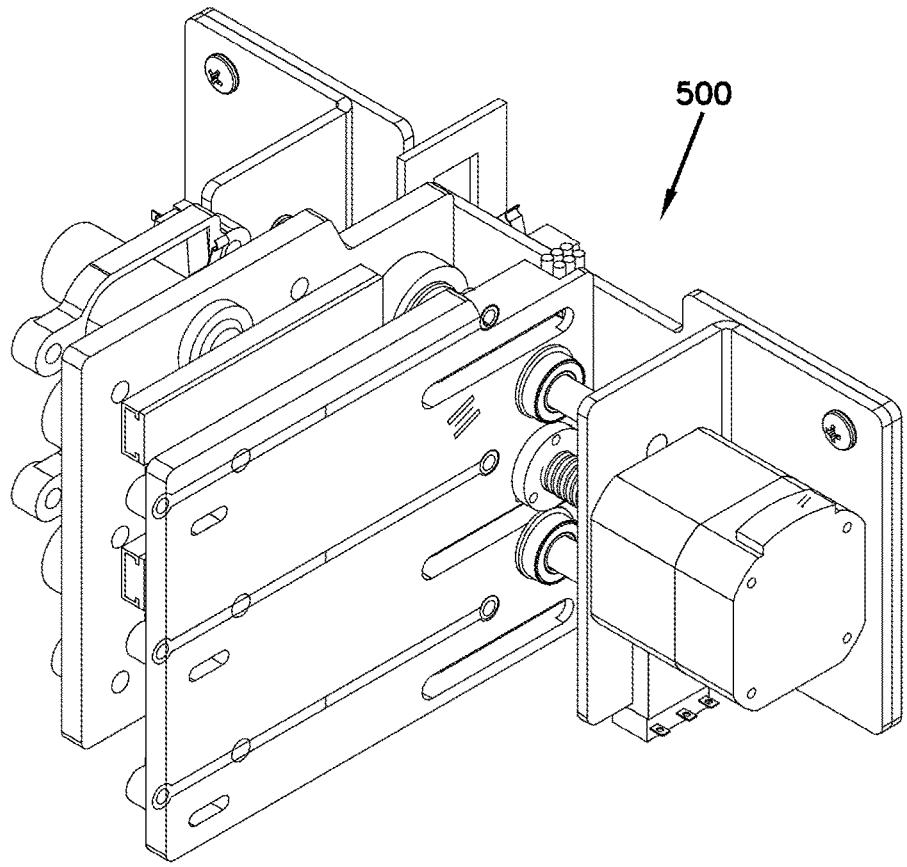
FIG. 31 is a further top perspective view of the vessel sealing assembly of FIG. 30.
Figure 32:
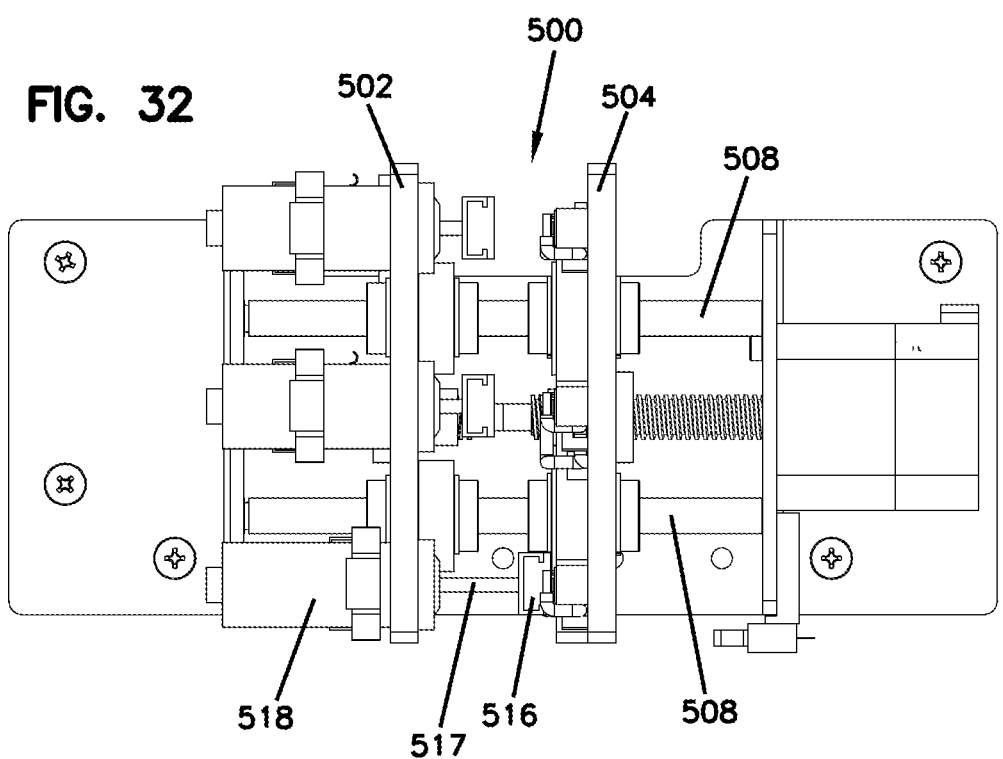
FIG. 32 is a front view of the vessel sealing assembly of FIG. 30.
Figure 33:
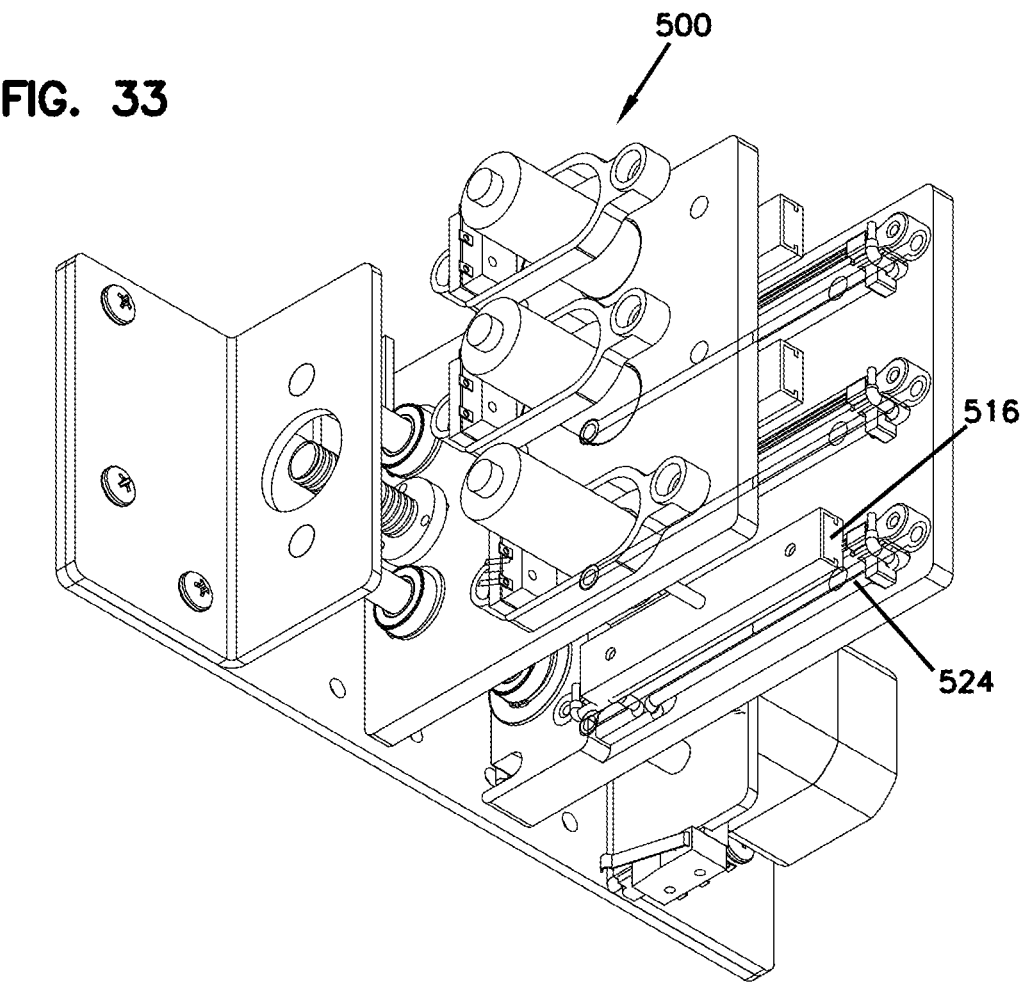
FIG. 33 is a bottom perspective view of the vessel sealing assembly of FIG. 30.
Figure 34:
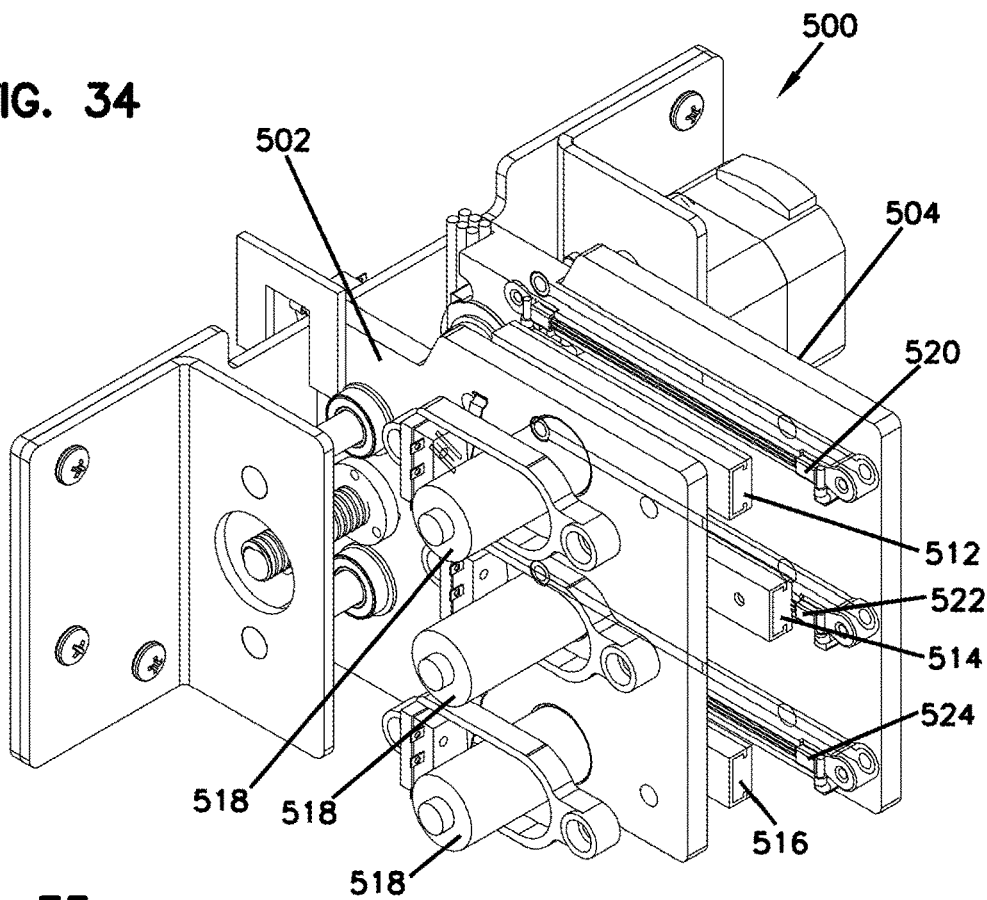
FIG. 34 is a top perspective view of the vessel sealing assembly of FIG. 26, the vessel sealing assembly being in a second activated configuration.
Figure 35:
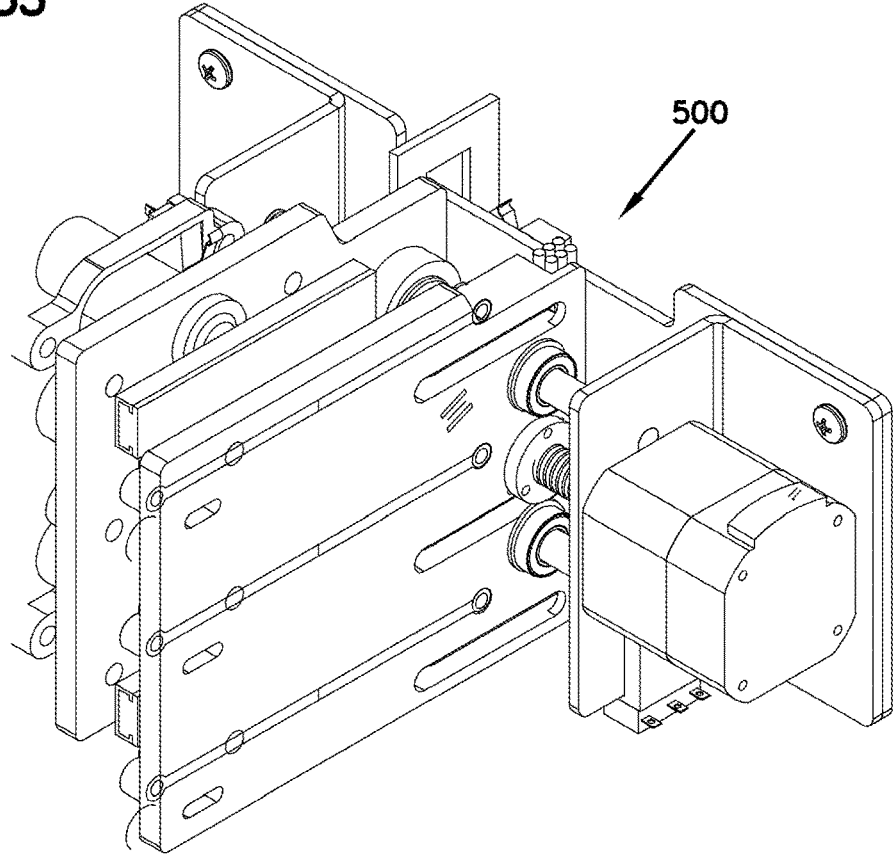
FIG. 35 is a further top perspective view of the vessel sealing assembly of FIG. 34.
Figure 36:
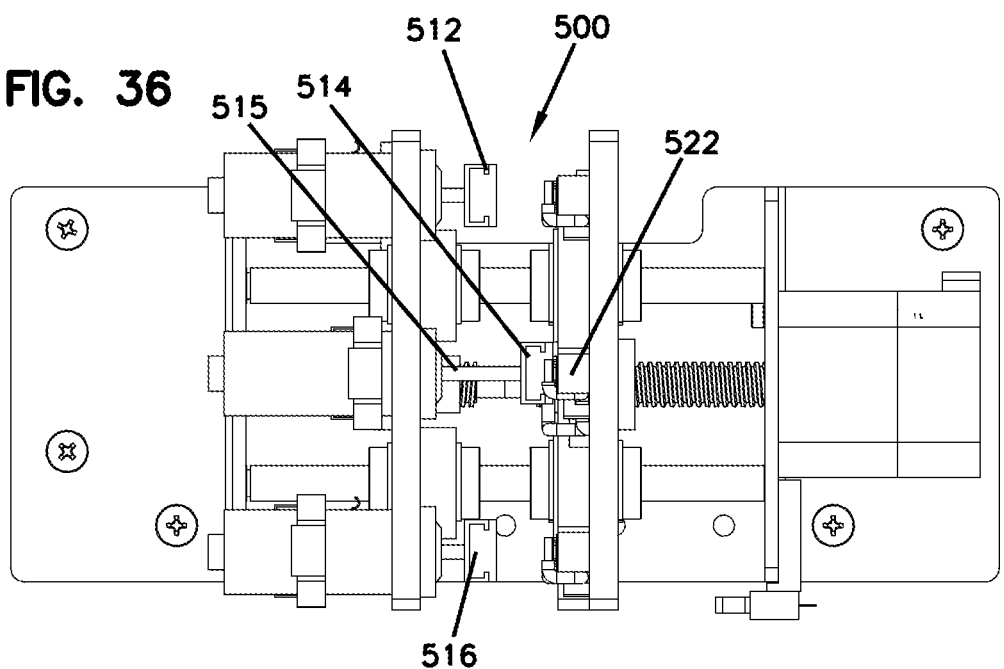
FIG. 36 is a front view of the vessel sealing assembly of FIG. 34.
Figure 37:
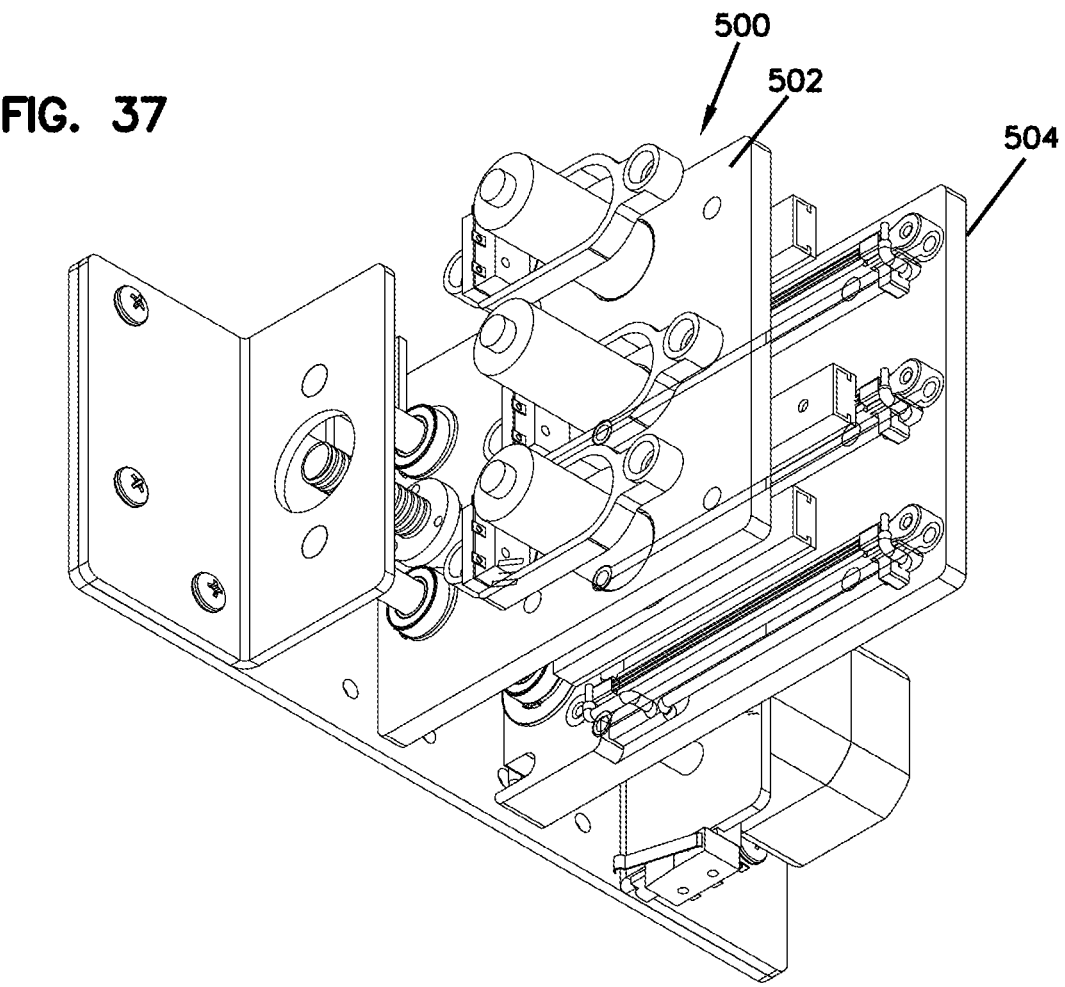
FIG. 37 is a bottom perspective view of the vessel sealing assembly of FIG. 34.
Figure 38:
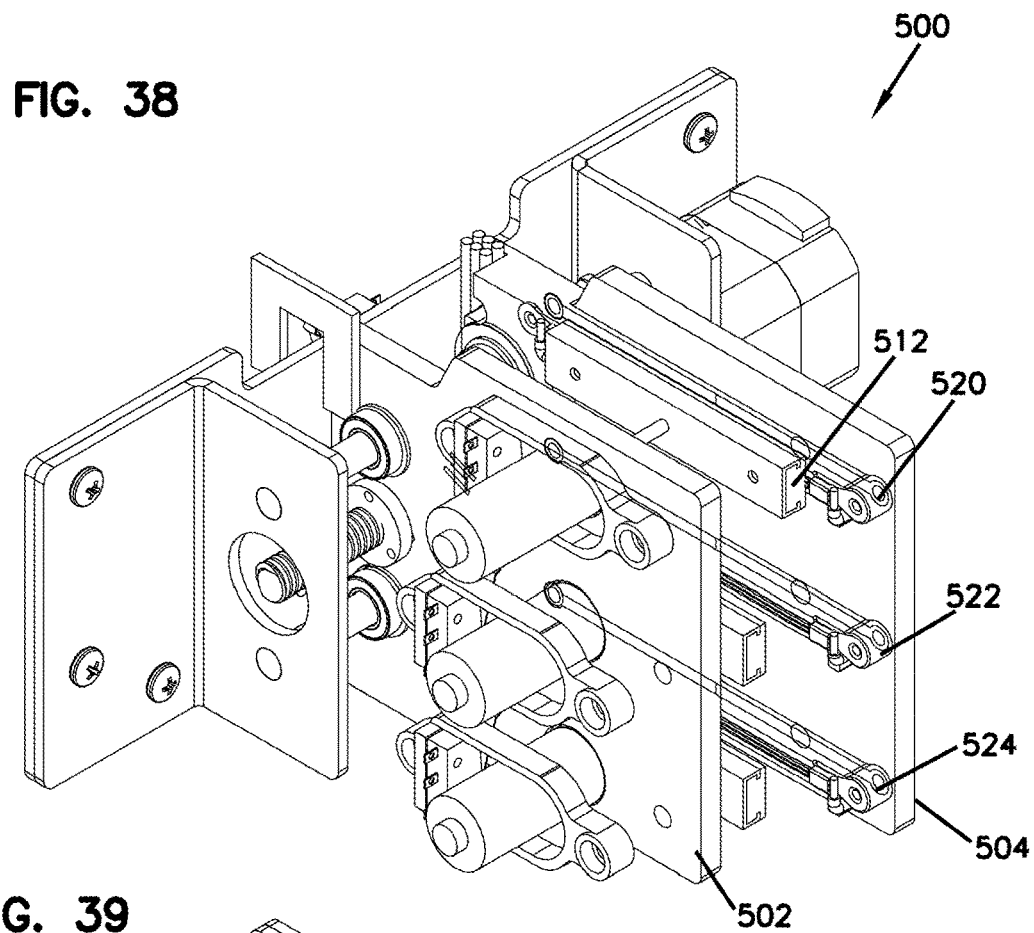
FIG. 38 is a top perspective view of the vessel sealing assembly of FIG. 26, the vessel sealing assembly being in a third activated configuration.
Figure 39:
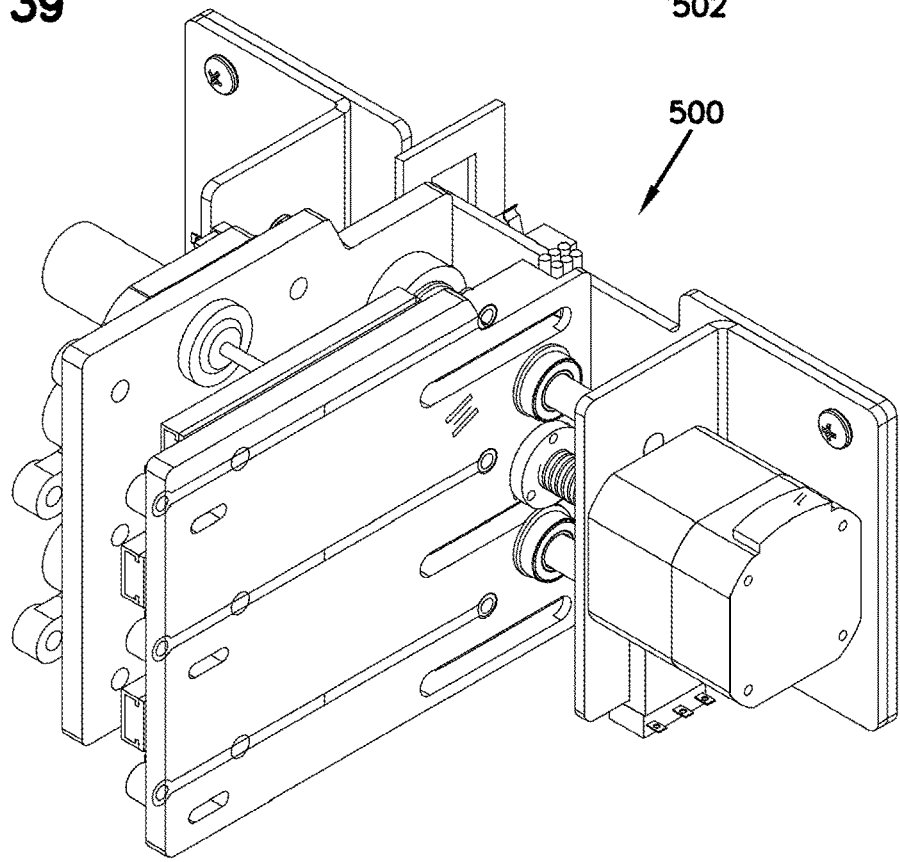
FIG. 39 is a further top perspective view of the vessel sealing assembly of FIG. 38.
Figure 40:
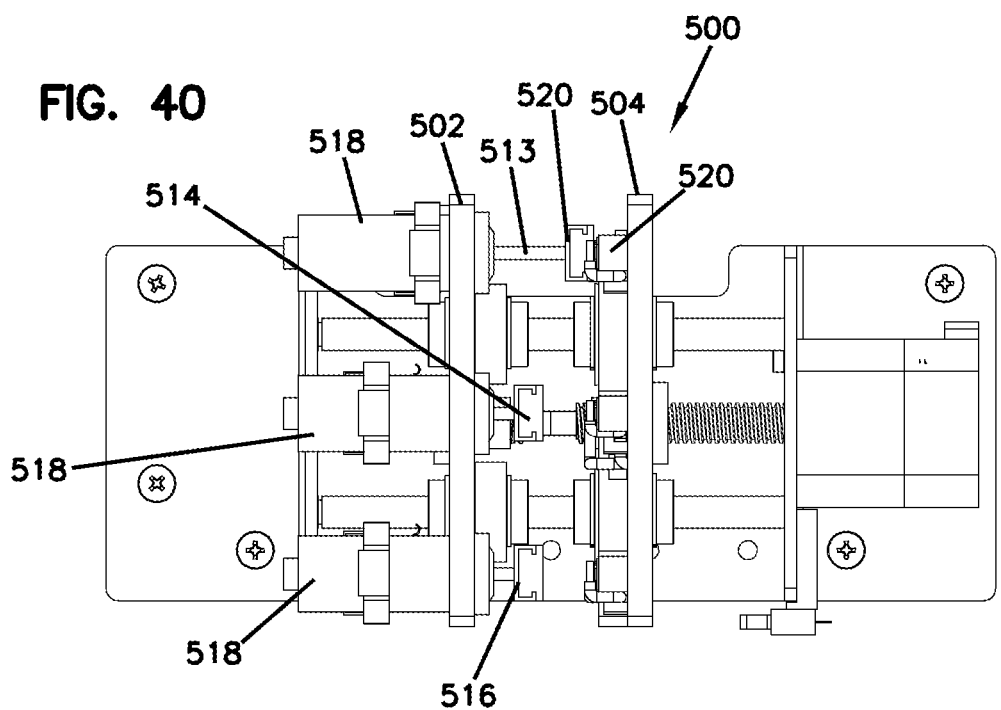
FIG. 40 is a front view of the vessel sealing assembly of FIG. 38.
Figure 41:
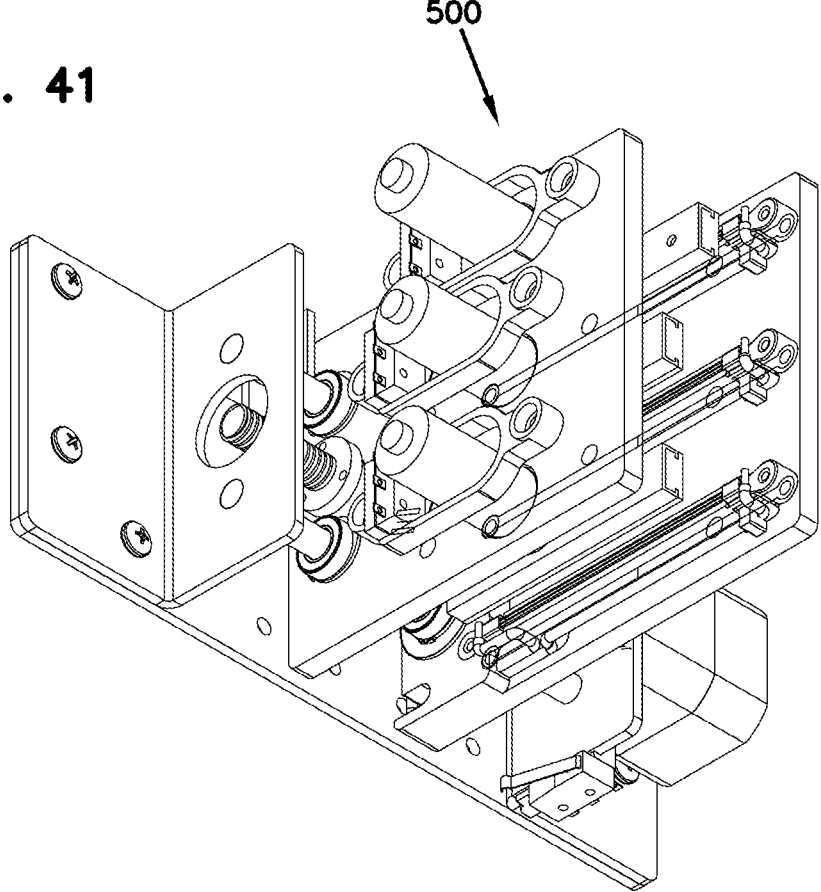
FIG. 41 is a bottom perspective view of the vessel sealing assembly of FIG. 38.
Figure 42:
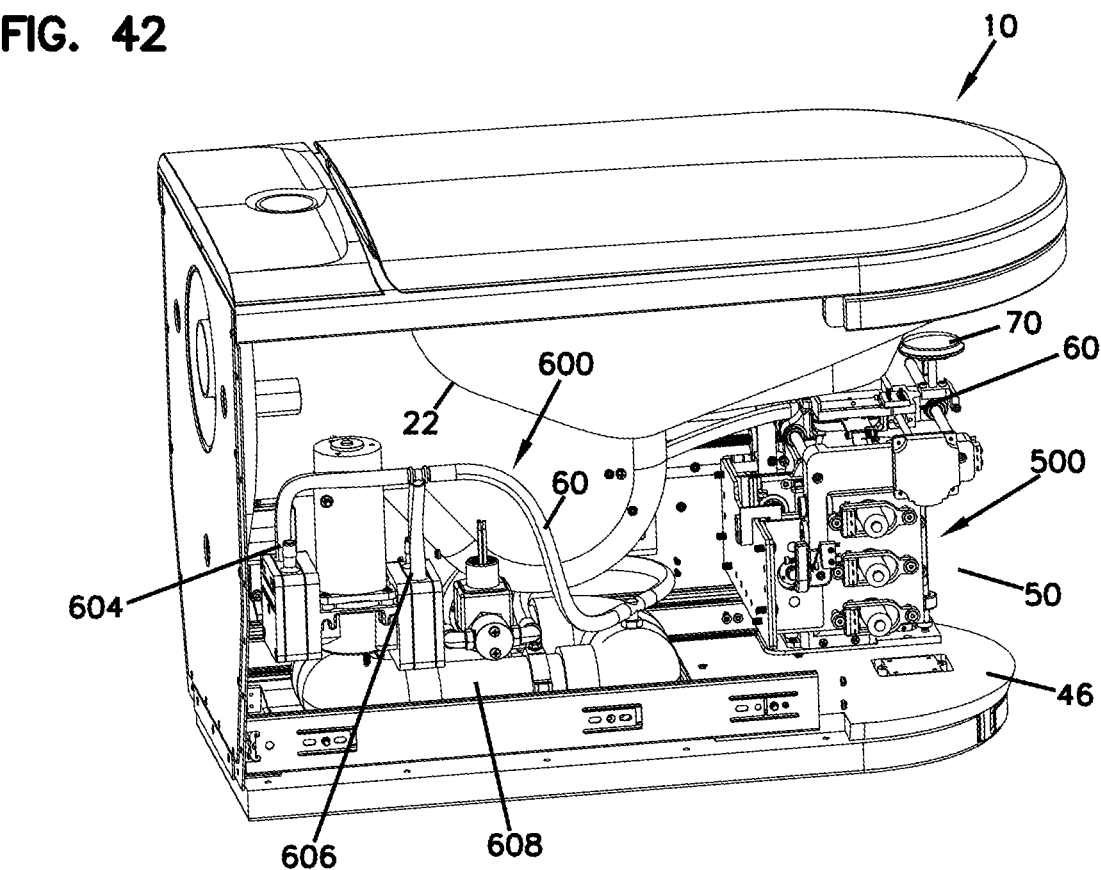
FIG. 42 is a perspective view of a portion of the interior of the biomaterial collection apparatus of FIG. 1.
Figure 43:
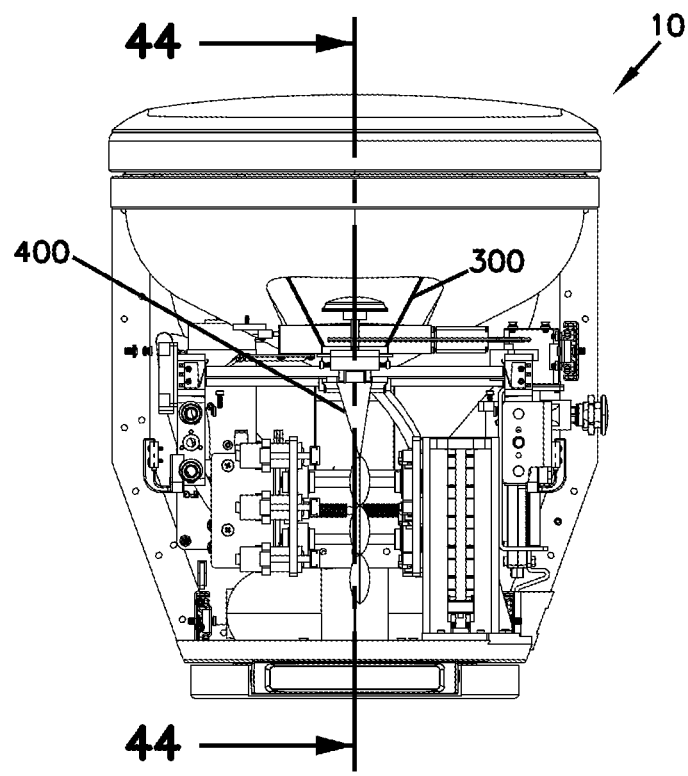
FIG. 43 is a front view of a portion of the biomaterial collection apparatus of FIG. 1.
Figure 44:
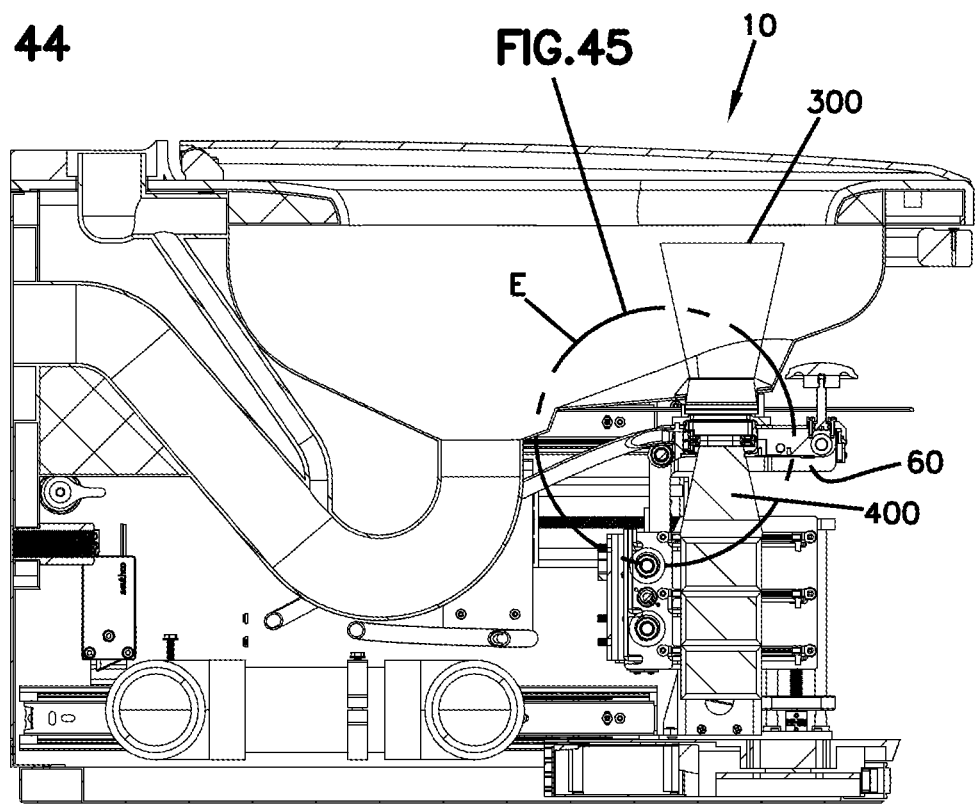
FIG. 44 is a cross-sectional view of a portion of the biomaterial collection apparatus of FIG. 1 taken along the line 44-44 in FIG. 43.
Figure 45:
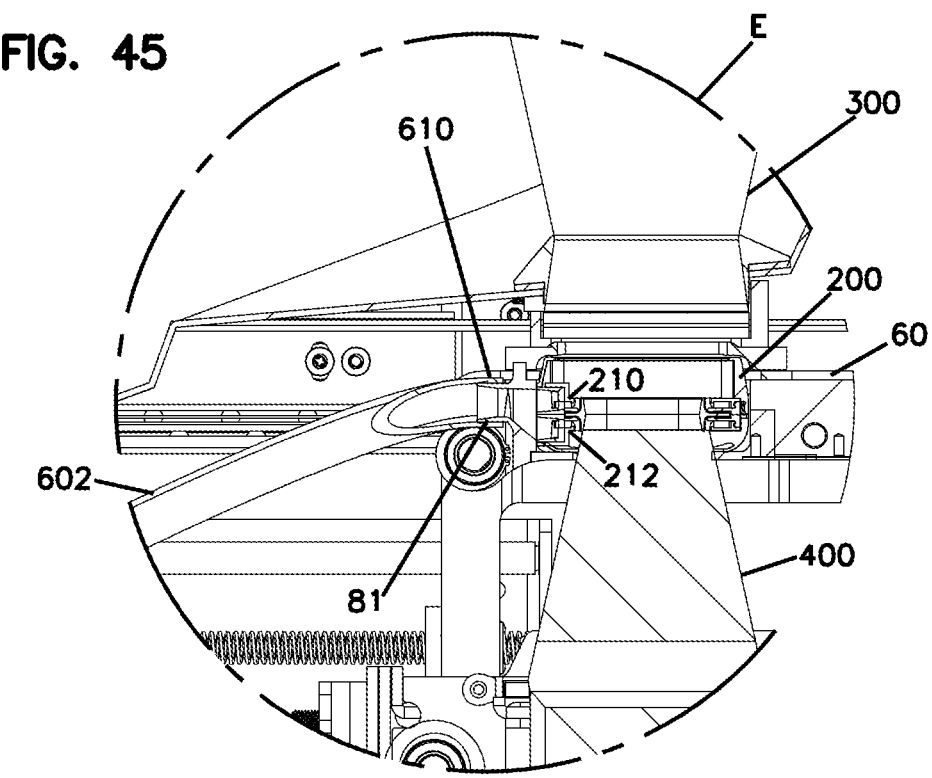
FIG. 45 is an enlarged view of the callout area E of FIG. 44.

Once the conduit 300 or the vessel 400 has been anchored as shown in FIG. 21B and the cartridge 200 fully assembled, the remaining uninflated material of the conduit 300 or the vessel 400 can be folded to fit neatly inside the chamber 204, 206 as shown, for example, in FIGS. 24-25. Once folded, in some examples the folded conduit or vessel is tucked under a lip defined by the first or second shell pieces or by the divider 234 such that no portion of the conduit 300 protrudes outside of the chamber 204, and such that no portion of the vessel 400 protrudes outside of the chamber 206 when the conduit 300 and the vessel 400, respectively, are not inflated.

It should be appreciated that the inflation opening of the collection vessel is an access point to an interior of the bladder or bladders of the collection vessel, the bladder(s) being defined by the interior surfaces of an outer flexible skin and an inner flexible skin of the collection vessel. The exterior surface of the inner flexible skin of the collection vessel defines the collection volume of the vessel and is the surface of the collection vessel that contacts the collected urine.

Similarly, one of an flexible inner skin or flexible outer skin of the collection conduit on a first side of the conduit's inflation opening is securely pressed between the frame members 230 and 232, while the other of the inner skin or outer skin of the collection conduit on an opposing side of the conduit's inflation opening is securely pressed between the divider 234 and the frame member 230. The pressing can occur between opposing surfaces of adjacent components of the cartridge. In addition, the collection conduit skin can be adhered to such surfaces, such as the surfaces 231, 235 showing in FIG. 21.

It should be appreciated that the inflation opening of the collection conduit is an access point to an interior of the bladder or bladders of the collection conduit, the bladder(s) being defined by the interior surfaces of an outer flexible skin and an inner flexible skin of the collection conduit. The exterior surface of the inner flexible skin of the collection conduit is the surface of the collection conduit that guides urine towards the collection vessel.

Lips 236, 238 protruding from the frame members 230 and 226, respectively, can further facilitate anchoring of the collection vessel and collection conduit and/or facilitate coupling of the anchoring unit components to each other.

The first shell piece 214 has on open top 215 through which the anchored collection conduit expands when inflated. The second shell piece 216 has on open bottom 217 through which the anchored collection vessel expands when inflated.

Referring now to FIGS. 24 and 25, an uninflated collection conduit 300 is shown schematically housed in the first chamber 204 prior to inflation. An uninflated collection vessel 400 is shown schematically housed in the second chamber 206 prior to inflation. In some examples, the collection conduit 300 and/or the collection vessel 400 can be folded up in their uninflated state for purposes of installation in their respective chambers of the cartridge 200.

Referring now to FIGS. 26-29, an example vessel sealing assembly 500 is disclosed. The assembly 500 can be housed in the sample processing volume 50 of the apparatus 10. In some examples, the assembly 500 is disposed between the receptacle 100 and the cartridge dispenser 74.

In operating principle, the vessel sealing assembly 500 is adapted to sequentially seal a plurality of portions of a deployed collection vessel, such as the collection vessel 400. The collection vessel 400 can be made of a heat sensitive material. The skin of the collection vessel 400 is pinched between a pair of horizontally aligned arms of the sealing assembly 500, at least one of which imparts sufficient heat to the collection vessel to create a heat seal. The location of the heat seal on the collection vessel can be controlled, and the collection vessel can be sealed in multiple locations to provide for multiple discrete sealed portions of the collection vessel.

Each sealed portion of the collection vessel can contain a portion of a subject's urine. The seals on the vessel can be made sequentially and progressively higher on the collection vessel as the urine is being collected in order to segregate collected volumes of urine one from another, and particularly in order to segregate a given subject's initial volume of collected urine from subsequently collected urine from the same subject.

Different sealing mechanisms can be employed to achieve the operating principles described. For example, a single pair of arms can be used to make all of the seals on a single collection vessel, wherein the arms and/or the collection vessel itself can be moved in the vertical direction during urination such that the arms horizontally align with different portions of the vessel during the course of the urination. In some examples, the arms can be configured to pivot into each other and away from each other to provide the sealing. In other examples, the arms are adapted to move only translationally, not rotationally, such that the entire width of each seal is formed at the same time. One or both of the arms can include a heating element, such as an electrical resistor, to provide for the heat sealing.

In the particular assembly 500 depicted, the assembly includes a pair of opposing plates 502 and 504 adapted to move towards and away from each other in the horizontal direction. A motor 510 can operate a drive 506 to move the plates 502 and 504 towards and away from each other in the horizontal direction along the horizontal guides 508. In this example, the vessel sealing assembly 500 is vertically stationary within the processing volume 50 of the apparatus 10.

Extending towards the plate 504 from the plate 502 are three arms 512, 514, and 516. The three arms 512, 514 and 516 can be independently activated (e.g., with a controller) by their respective solenoids 518. When a given solenoid 518 fires, it causes its corresponding arm 512 514 or 516 to move horizontally towards the plate 504. When the solenoid 518 switches off, the corresponding arm retracts to the resting position shown in FIGS. 26-29.

Each of the three arms 512, 514, and 516 is horizontally aligned with a corresponding heating arm 520, 522, and 524 extending towards the plate 502 from the plate 504. In this example, the heating arms 520, 522, and 524 remain stationary with respect to the plate 504. Each of the heating arms 520, 522, and 524 includes a heating element 526 connected to a power source. In operation, a horizontally aligned arm/heating arm pair press a portion of a collection vessel to seal it thereby. In some examples, each of the arms 512, 514 and 516 can include a heat resistant compressible pad 530 to ensure sufficient contact and force by the arm/heating arm pair on the vessel to achieve an adequate seal.

Referring now to FIGS. 30-33, the vessel sealing assembly 500 is shown in a first activated configuration. The plates 502 and 504 have been driven horizontally towards each such that they are close enough for the arms 512, 514, and 516 to reach and make contact with the corresponding heating arms 520, 522, and 524 when the corresponding solenoid 518 is activated but not so close as to inhibit urine capture by the collection vessel 400.

In the first activated configuration, shown in FIGS. 30-33, only the lowermost solenoid 518 is fired to activate the lowermost arm 516 to extend (via the extension shaft 517) horizontally towards the plate 504 and thereby seal off a bottom portion of a collection vessel, i.e., a portion of the vessel below the seal formed by the pressing of the vessel between the arm 516 and the heating arm 524 and, more specifically, between the heating element 526 of the heating arm 524 and the compressible pad 530 of the arm 516.

Referring now to FIGS. 34-37, the vessel sealing assembly 500 is shown in a second activated configuration. The plates 502 and 504 remain close enough to each other for the arms 512, 514, and 516 to reach and make contact with the corresponding heating arms 520, 522, and 524 when the corresponding solenoid 518 is activated. The lowermost solenoid 518 is switched off and the arm 516 has retracted.

In the second activated configuration, shown in FIGS. 34-37 and typically performed subsequent to the first activated configuration for a given urine sample capture, only the middle solenoid 518 is fired to activate the middle arm 514 to extend (via the extension shaft 515) horizontally towards the plate 504 and thereby seal off a second portion of a collection vessel, i.e., a portion of the vessel immediately above the first seal, by pressing of the vessel between the arm 514 and the heating arm 522 and, more specifically, between the heating element 526 of the heating arm 522 and the compressible pad 530 of the arm 514.

Referring now to FIGS. 38-41, the vessel sealing assembly 500 is shown in a third activated configuration. The plates 502 and 504 remain close enough to each other for the arms 512, 514, and 516 to reach and make contact with the corresponding heating arms 520, 522, and 524 when the corresponding solenoid 518 is activated. The lower two solenoids 518 are switched off and the arm 514 has retracted.

In the third activated configuration, shown in FIGS. 38-41 and typically performed subsequent to the second activated configuration for a given urine sample capture, only the top solenoid 518 is fired to activate the top arm 512 to extend (via the extension shaft 513) horizontally towards the plate 504 and thereby seal off a third portion of a collection vessel, i.e., a portion of the vessel immediately above the second seal, by pressing of the vessel between the arm 512 and the heating arm 520 and, more specifically, between the heating element 526 of the heating arm 520 and the compressible pad 530 of the arm 512.

Following creation of the third seal on the collection vessel via the third activated configuration of the vessel sealing assembly 500, the arm 520 can retract following shutting off of its solenoid 518, and the plates 502 and 504 can be driven apart horizontally to return the assembly 500 to the configuration of FIGS. 26-29.

Referring now to FIGS. 42-45, the apparatus 10 is shown in a configuration following collection and sealing of a urine sample in a collection vessel 400 that has been deployed from a cartridge 200. A collection conduit 300 is also shown schematically deployed from the cartridge 200.

A pneumatic system 600 is housed in the processing volume 50 of the apparatus 10. The pneumatic system 600 is adapted to inflate and/or expand, via air pressure differential, the collection conduit 300 and the collection vessel 400 when it is time to receive a urine sample from a subject. The pneumatic system can include, e.g., one or more pumps, motors, accumulators, compressors, valves, hoses, and/or nozzles.

The pneumatic system's hose outlet or nozzle can be adapted to releasably mate with the air inlets 210 and 212 of the cartridge 200 and/or with the inlet 81 of the conveyance assembly 60, which is in turn in gaseous communication with the air inlets 210 and 212 of the cartridge 200, the discharged air/gas stream being divided between the two air inlets 210 and 212.

In some examples, the air outlet(s) of the pneumatic system 600 are positioned to mate with the inlet 81 of the conveyance assembly 60 automatically upon the cartridge's moving into a urine sample collection position below the collection port. In other examples, one or more motorized drives can control the positioning of the air outlet(s) of the pneumatic system 600 and cause the air outlet(s) of the pneumatic system 600 to move towards and engage the inlet 81 of the conveyance assembly 60, and also to move away from and disengage from the conveyance assembly 60 when following a urine sample collection.

Referring now to features of the pneumatic system 600 shown in FIGS. 42-45, the example pneumatic system 600 includes a compressor 608, and a hose 602 connected to an air (or other gaseous substance) discharge port 604 and an air (or other gaseous substance) suction port 606. A distal end 610 of the hose 602 mates with, and forms a hermetic seal around, the inlet 81 of the conveyance assembly 60. Air/gas is discharged from the pneumatic system 600 via the distal end 610 of the hose 602. The gas then inflates the collection conduit 300 via the air inlet 210 and the collection vessel 400 via the air inlet 212.

It should be appreciated that inflation of the collection conduit 300 and collection vessel 400 can occur simultaneously. In some examples, the pneumatic system 600 is adapted to continuously discharge air to inflate the collection vessel 400 and the collection conduit 300 during a urine collection, i.e., until the hose 602 is disengaged from the conveyance assembly 60. In other examples, the collection conduit 300 and/or the collection vessel 400 can include a valve to prevent or reduce deflation during a urine collection and, once the collection conduit 300 and/or the collection vessel 400 have been inflated, the hose 602 can disengage from the conveyance assembly 60 prior to completion of the sample collection.

Referring now to FIGS. 46-49, the conveyance assembly 60 has positioned the cartridge 200 to align the vertical expansion of the collection vessel and collection conduit with the collection port 40 in the toilet bowl 22. The hose 602 has been hooked up to the conveyance assembly 60 and the collection conduit 300 and the collection vessel 400 have been inflated. As the collection conduit 300 inflates, it deploys upwards from the cartridge 200 and extends upwards through the collection port 40 into the toilet bowl 22. As the collection vessel 400 inflates, it deploys downwards from the cartridge 200 into the processing volume 50 of the apparatus 10.

The collection vessel 400 can include an inner skin and an outer skin, the interior surfaces of which define one or more bladders therebetween that can be inflated, the exterior surface of the inner skin defining the interior collection volume of the vessel 400.

Figure 46:
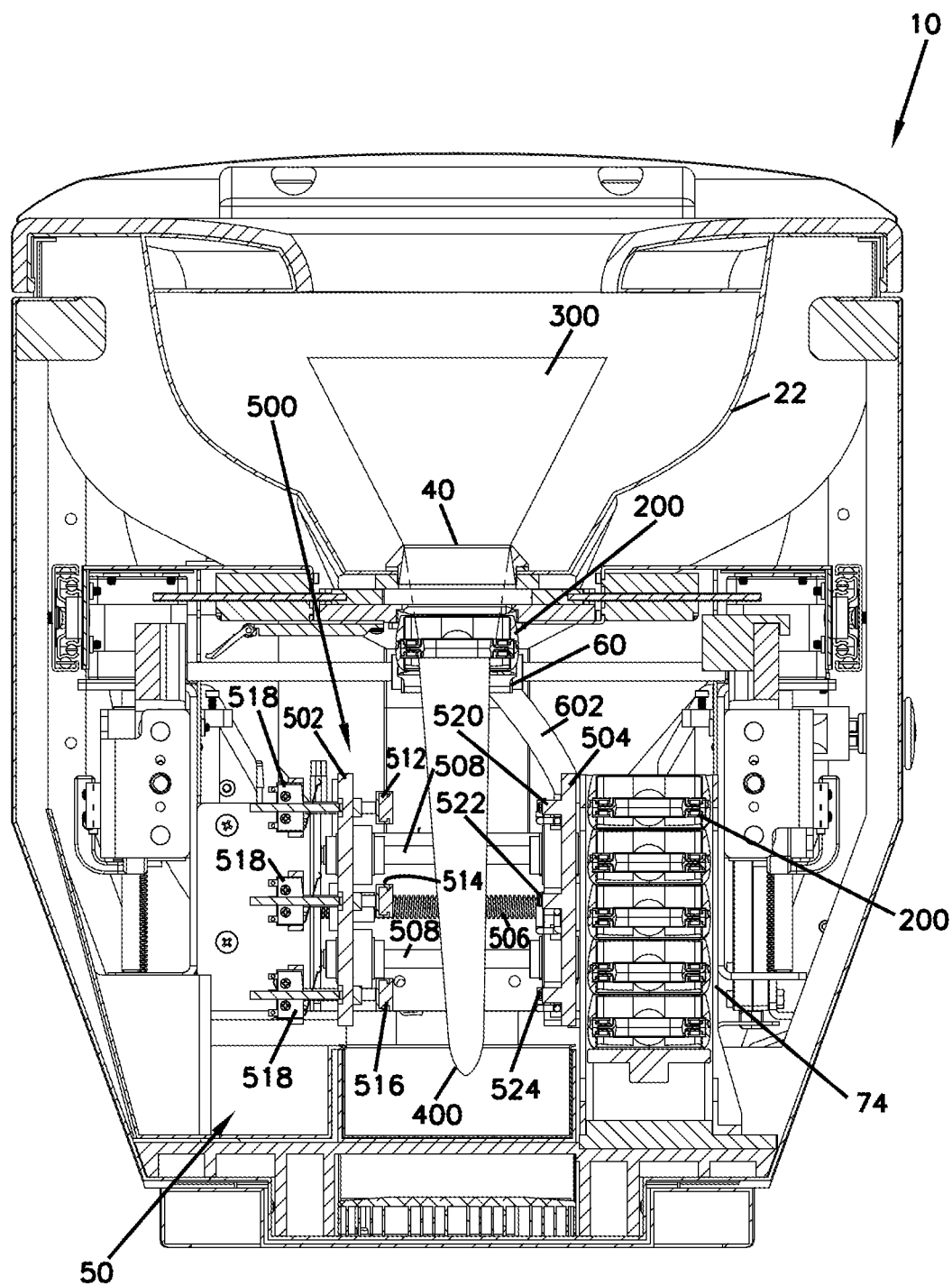
FIG. 46 is a front view of a portion of the interior of the apparatus of FIG. 1, the apparatus being in an initial collection configuration.
Figure 47:
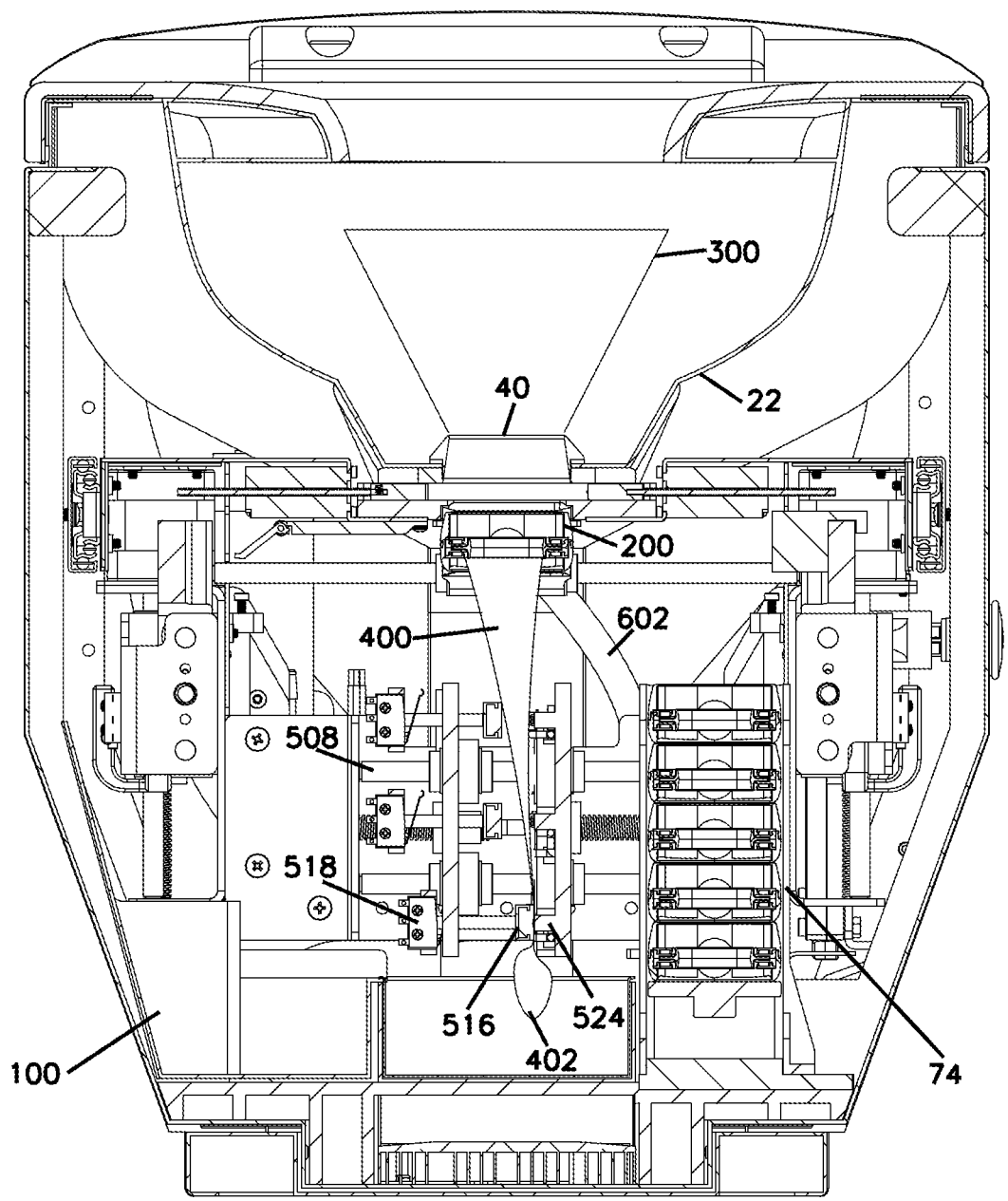
FIG. 47 is front view of the apparatus portion of FIG. 46, the apparatus being in first sealing configuration, the first sealing configuration being subsequent to the configuration of FIG. 46.

Referring to FIGS. 46 and 47, when the apparatus 10 is ready to receive a urine sample, the plates 502 and 504 of the vessel sealing assembly 500 move horizontally towards each other. At that point, urine is captured by the collection conduit 300 and flows into the collection vessel 400. A sensor 61 (FIG. 16) can detect when a threshold volume of urine has been captured by the vessel 400, triggering the solenoid 518 to activate the arm 516 which forms a heat seal on the vessel 400 by pressing the vessel 400 between the arm 516 and the heating arm 524. The seal creates a first sealed vessel subunit 402 containing an initial portion of the subject's urine stream. Alternatively, as described above, the weight sensor 95 of the cartridge basket 72 can provide a signal to activate the arm 516 which forms a heat seal on the vessel 400 by pressing the vessel 400 between the arm 516 and the heating arm 524.

Figure 48:
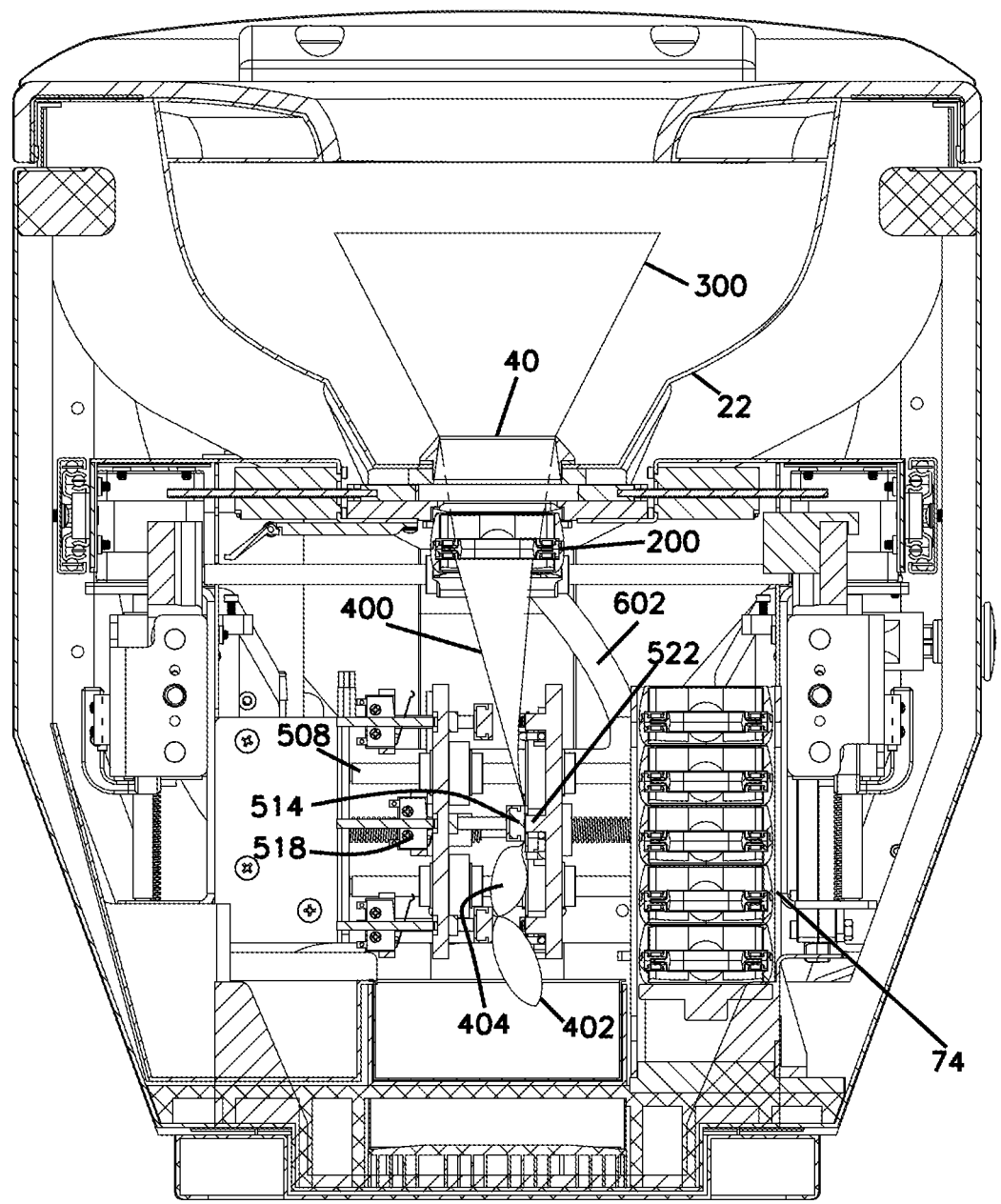
FIG. 48 is a front view of the apparatus of FIG. 46, the apparatus being in a second sealing configuration, the second sealing configuration being subsequent to the configuration of FIG. 47.

Referring to FIG. 48, subsequent to the creation of the first sealed vessel subunit 402, a sensor (e.g., the sensor 61) detects when a further threshold volume of urine has been captured by the vessel 400, triggering the solenoid 518 to activate the arm 514 which forms a heat seal on the vessel 400 by pressing the vessel 400 between the arm 514 and the heating arm 522. The seal creates a second sealed vessel subunit 404 containing a second portion of the subject's urine stream. Alternatively, as described above, the weight sensor 95 of the cartridge basket 72 can provide a signal to activate the arm 514 which forms a heat seal on the vessel 400 by pressing the vessel 400 between the arm 514 and the heating arm 522.

In this example the first and second sealed vessel subunits 402 and 404 remain attached to each other. In other examples the first and second sealed vessel subunits 402 and 404 are severed from each other (e.g., with a blade or with a heating element that melts the junction between the subunits) without compromising the seal of each subunit.

Figure 49:
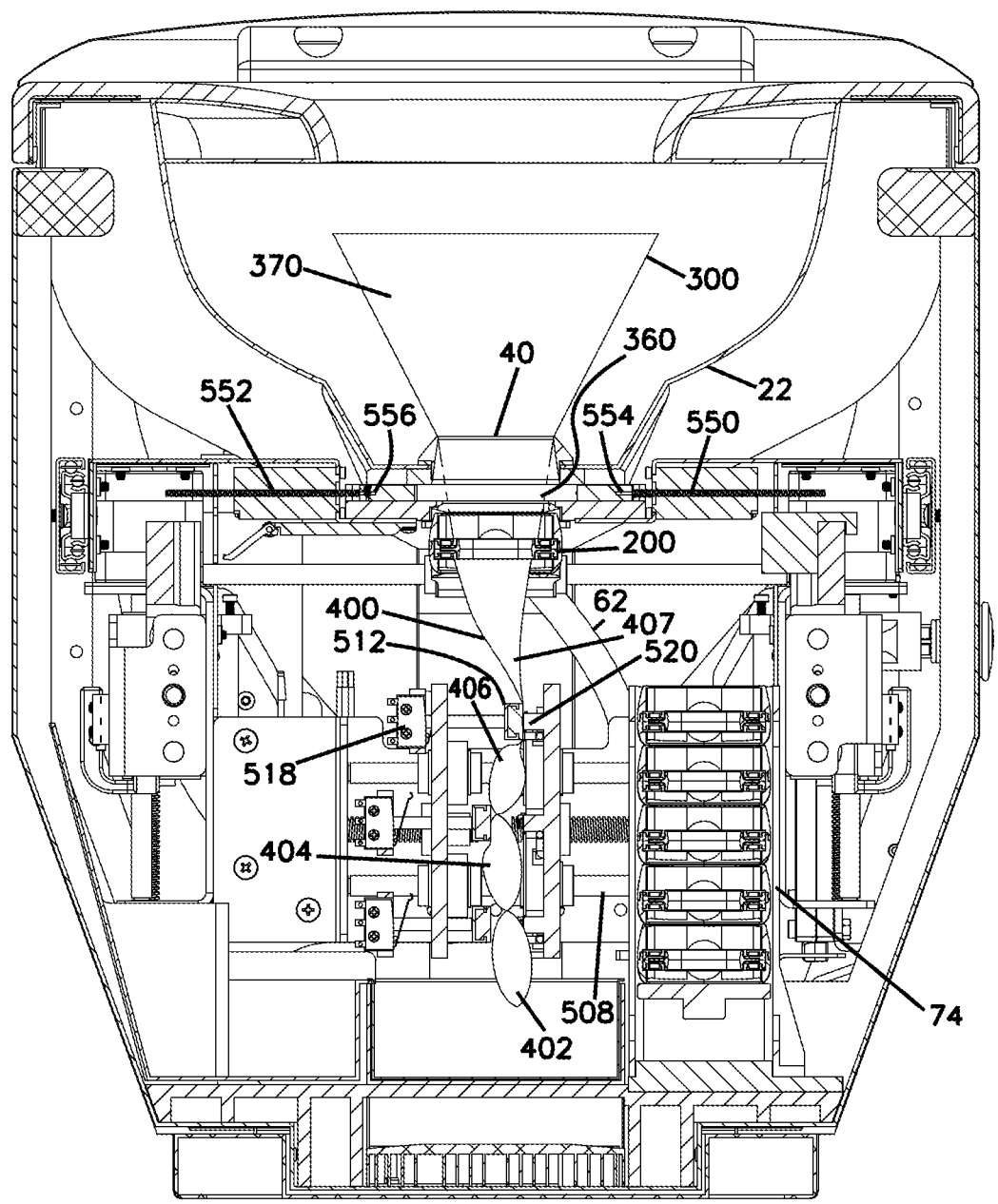
FIG. 49 is a front view of the apparatus of FIG. 46, the apparatus being in a third sealing configuration, the third sealing configuration being subsequent to the configuration of FIG. 48.

Referring to FIG. 49, subsequent to the creation of the first and second sealed vessel subunits 402 and 404, a sensor (e.g., the sensor 61) detects when urination has been completed (i.e., no further urine is captured by the vessel 400), triggering the solenoid 518 to activate the arm 512 which forms a heat seal on the vessel 400 by pressing the vessel 400 between the arm 512 and the heating arm 520. The seal creates a third sealed vessel subunit 406 containing a third and final portion of the subject's urine stream. Alternatively, as described above, the weight sensor 95 of the cartridge basket 72 can provide a signal to activate the arm 512 which forms a heat seal on the vessel 400 by pressing the vessel 400 between the arm 512 and the heating arm 520.

In addition, in some examples at least the heating arm 520 includes a cutting element such as a horizontally extending metal wire or blade adapted to cooperate with the arm 512 to cut the seal on the vessel 400 formed between the heating arm 520 and the arm 512 in a substantially horizontal incision such that a portion of the seal is above the incision and a portion of the seal is below the incision, causing the interconnected sealed vessel subunits to drop.

In this example, the first, second and third sealed vessel subunits 402, 404, and 406 remain attached to one another for retrieval by an operator of the apparatus. In other examples one or more of the subunits are severed from the others (e.g., with a blade or with a heating element that melts the junction between the subunits) without compromising the seal of each subunit. For example, one or both of the other heating arms 522, 524 can also include a cutting element as just described to cooperate with the corresponding arm, 514, 516 for purposes of severing one or both of the corresponding sealed vessel subunits 402, 404, from each other or from the subunit 406.

Following completion of the urine capture and sealing of the subunits, an upper portion 407 of the collection vessel 400 above the third vessel subunit 406 can be cut, e.g., by hand, with one or more blades, or one or more heating elements, such that the subunits 402, 404 and 406 are retrievable from the apparatus 10 by an operator. Optionally, the subunits can be labeled, e.g., to indicate the subject and/or the initial urine stream subunit, etc. Once retrieved, the urine contained in one or more of the subunits can be test for the presence of any of a number of different compounds.

In some examples, a pair of sealing plates 550 and 552 (FIG. 49) can be provided above the cartridge 200. The sealing plates 550 and 552 are adapted to move horizontally, e.g., on tracks, towards and away from each other.

At some point after urination is complete (e.g., the patient leaves the collection room and an operator of the apparatus initiates a sample retrieval process), excess urine that may have been captured above the uppermost seal formed by the heating arm 520 and the arm 518 within an upper portion 407 of the vessel 400 must be disposed.

To dispose of such excess urine in a sanitary fashion, the sealing plates 550 and 552 can be activated to seal the conduit 300 above a lower portion 360 of the conduit 300 and below an upper portion 370 of the conduit 300. One of the sealing plates 550, 552 can also include a cutting element, such as a wire or a blade, to sever the conduit 300 between an upper portion and a lower portion of the seal formed by the sealing plates 550 and 552, creating a sealed pouch of excess urine that includes the upper portion 407 of the vessel 400 and the lower portion 360 of the conduit 300. For example, the opposing edges 554 and 556 of the sealing plates 550 and 552 can cooperate in the same manner as the heating arm 520 and the arm 518 and include the same heating and cutting features as the heating arm 520 and the arm 518.

The sealed off pouch of excess urine is still anchored to the cartridge 200 and can be disposed of along with the remainder of the cartridge. Meanwhile, the severed portion 370 of the conduit 300 can be flushed down the sewage port 26 along with any additional urine captured therein.

Following severance of the vessel subunits 402, 404, and 406 from the upper portion 407 of the vessel 400, the hose 602 can be disengaged from the conveyance assembly 60, and the conveyance subassembly is moved horizontally to a position above the receptacle 100 where the used cartridge 200 is released into the receptacle 100. In some examples in which the sealing plates 550 and 552, e.g., do not include a cutting element, this horizontal movement of the conveyance assembly 60 can cause the upper portion 370 of the collection conduit 300 to break off into the toilet bowl 22 from which it can be flushed down the sewage port 26.

Figure 50:
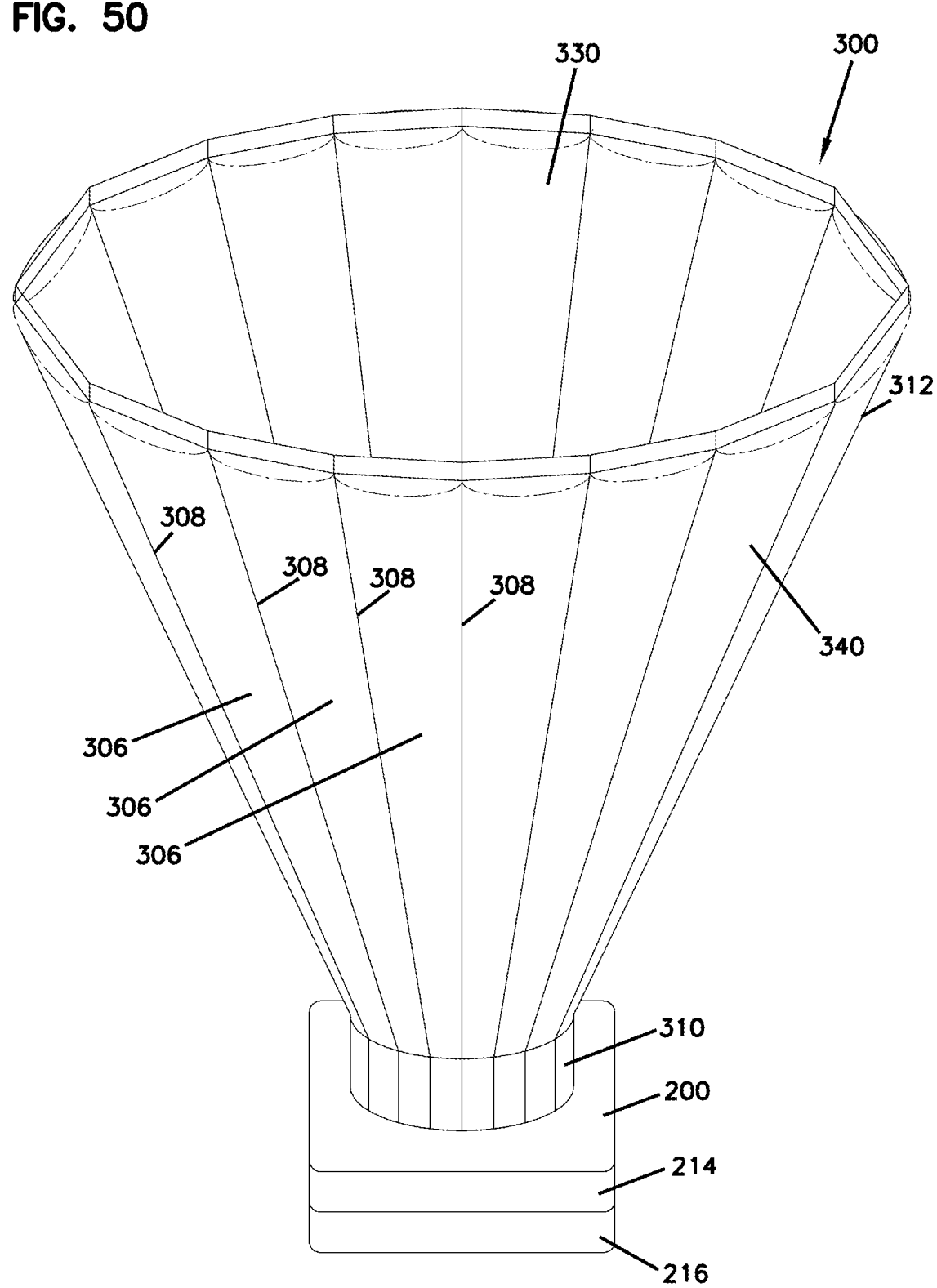
FIG. 50 is a perspective view of an example inflated collection conduit deployed from an example cartridge in accordance with the present disclosure, the cartridge being shown schematically.

Referring now to FIG. 50, an example collection conduit 300 that can be deployed from a cartridge 200 (shown schematically) in accordance with the present disclosure is shown and substantially defines a funnel. The funnel includes the flexible inner skin 330 and the flexible outer skin 340 described above, the interior surfaces of which together define a plurality of inflatable bladders 306, which are segregated from each other and/or reinforced by seams or baffles 308. A relatively narrow neck region 310 of the collection conduit 300 is adapted to fit through the collection port 40. A funnel region 312 extends and expands upwardly from the neck region 310.

As used herein, the term "vertical" means substantially aligned with the force of gravity on Earth, and the term "horizontal" means substantially perpendicular to the force of gravity on Earth.

While the above is a complete description of certain embodiments of the invention, various alternatives, modifications, and equivalents may be used. Therefore, the above description should not be taken as limiting the scope of the invention as defined by the appended claims.

What is claimed is:

1. A method for collecting a urine sample in a collection vessel, comprising:
   providing a cartridge having a housing defining at least one chamber, the at least one chamber enclosing the entirety of the collection vessel and the entirety of a funnel;
   pumping gas into the cartridge, including into the vessel and into the funnel simultaneously, to deploy the collection vessel to a position below the housing and to deploy the funnel to a position above the housing;
   detecting, subsequent to the pumping, an initial volume of urine captured by the deployed vessel through the funnel, the initial volume being less than a total volume of urine captured by the vessel;
   sealing, in response to the detecting and before the total volume of urine is captured, the initial volume in a first portion of the vessel; and
   capturing, subsequent to the sealing, a first non-initial volume of urine in a second portion of the vessel.

2. The method of claim 1, further comprising sealing, subsequent to the capturing, of the first non-initial volume of urine in the second portion of the vessel.

3. The method of claim 2, further comprising:
   capturing, subsequent to the sealing of the second portion of the vessel, a second non-initial volume of urine in a third portion of the vessel; and
   sealing, subsequent to the capturing of the second non-initial volume of urine, of the second non-initial volume of urine in the third portion of the vessel;
   wherein the total volume of urine is equivalent to a sum of the initial volume, the first non-initial volume, and the second non-initial volume.

4. The method of claim 3,
   wherein the sealing of the initial volume of urine is performed by a first pair of sealing arms that releasably press and seal the collection vessel;
   wherein the sealing of the first non-initial volume of urine is performed by a second pair of sealing arms that releasably press and seal the collection vessel; and
   wherein the sealing of the second non-initial volume of urine is performed by a third pair of sealing arms that releaseably press and seal the collection vessel.

5. The method of claim 4, wherein the sealings are performed by the first, second and third pairs of sealing arms activated in chronological sequence.

6. The method of claim 4, wherein each of the first, second and third pairs of sealing arms includes a heating element and a compressible pad.

7. The method of claim 6, wherein each of the first, second, and third pairs of sealing arms is activated by a solenoid.

8. The method of claim 7, wherein, for each of the pairs of the sealing arms, one of the sealing arms is coupled to an extension shaft that extends from, and retracts towards, a plate to which the sealing arm is coupled.

9. The method of claim 1, further comprising moving a pair of plates towards each other before the detecting, wherein each of the plates supports at least one sealing arm.

10. The method of claim 9, further comprising moving the pair of plates away from each other after capturing the total volume of urine in the vessel.

11. The method of claim 1, wherein the detecting is performed by one or more of a light sensor, a heat sensor, a weight sensor, or a volume sensor.

12. A method for collecting urine of a subject's urination, comprising:
   providing a cartridge having a housing containing a vessel and a funnel;
   pumping gas into the cartridge to deploy the vessel to a position below the housing and to deploy the funnel to a position above the housing;
   capturing, in the deployed vessel, through the funnel, and subsequent to the pumping, an initial volume of urine from the urination, the initial volume being less than a total volume of urine of the urination;
   automatically detecting that the initial volume of urine from the urination has been captured by the vessel;
   automatically sealing the vessel in response to the detecting and before the total volume of urine of the urination is captured; and capturing, subsequent to the sealing, a non-initial volume of urine of the urination.

13. The method of claim 12, wherein the detecting is performed by at least one of a light sensor, a heat sensor, a weight sensor, and a volume sensor.

* * * * *